(12) United States Patent
Okajima et al.

(10) Patent No.: US 12,312,641 B2
(45) Date of Patent: May 27, 2025

(54) SENSITIVITY MARKER FOR ANTIBODY-DRUG CONJUGATE

(71) Applicant: DAIICHI SANKYO COMPANY, LIMITED, Tokyo (JP)

(72) Inventors: Daisuke Okajima, Tokyo (JP); Satoru Yasuda, Tokyo (JP); Kei Enomoto, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 1071 days.

(21) Appl. No.: 17/269,615

(22) PCT Filed: Aug. 22, 2019

(86) PCT No.: PCT/JP2019/032773
§ 371 (c)(1),
(2) Date: Feb. 19, 2021

(87) PCT Pub. No.: WO2020/040245
PCT Pub. Date: Feb. 27, 2020

(65) Prior Publication Data
US 2021/0340628 A1 Nov. 4, 2021

(30) Foreign Application Priority Data
Aug. 23, 2018 (JP) .................. 2018-156449

(51) Int. Cl.
*C12Q 1/6886* (2018.01)
*G01N 33/574* (2006.01)
*G01N 30/88* (2006.01)

(52) U.S. Cl.
CPC ......... *C12Q 1/6886* (2013.01); *G01N 33/574* (2013.01); *C12Q 2600/106* (2013.01); *C12Q 2600/158* (2013.01); *G01N 2030/8827* (2013.01)

(58) Field of Classification Search
CPC ............ C12Q 1/6886; C12Q 2600/106; C12Q 2600/158; G01N 33/574; G01N 2800/52; G01N 2030/8827
See application file for complete search history.

(56) References Cited

U.S. PATENT DOCUMENTS

| 7,999,083 B2 | 8/2011 | Govindan et al. |
| 2016/0297890 A1 | 10/2016 | Agatsuma et al. |

FOREIGN PATENT DOCUMENTS

| WO | WO-03/074566 A2 | 9/2003 |
| WO | WO-2008/144891 A1 | 12/2008 |
| WO | WO-2011/068845 A1 | 6/2011 |
| WO | WO-2011/145744 A1 | 11/2011 |
| WO | WO-2011/155579 A1 | 12/2011 |
| WO | WO-2013/068946 A2 | 5/2013 |
| WO | WO-2013/077458 A1 | 5/2013 |
| WO | WO-2014/057687 A1 | 4/2014 |
| WO | WO-2014/061277 A1 | 4/2014 |
| WO | WO-2015/098099 A1 | 7/2015 |
| WO | WO-2015/115091 A1 | 8/2015 |
| WO | WO-2015/146132 A1 | 10/2015 |
| WO | WO-2015/155976 A1 | 10/2015 |
| WO | WO-2015155998 A1 * | 10/2015 ......... A61K 31/4745 |

OTHER PUBLICATIONS

Fenn et al., Drugs Today (Barc), 2019, 55(9): 575-585.*
Mollaoglu et al., Cancer Cell, Feb. 13, 2017, 31:270-285.*
Anders, S. et al., "Differential expression analysis for sequence count data", Genome Biology, vol. No. 11, Issue No. R106, 2010, 12 pages.
Berghoff, B. et al., "RNA-sequence data normalization through in silico prediction of reference genes: the bacterial response to DNA damage as case study", BioData Mining, vol. No. 10, Issue No. 30, 2017, 20 pages.
Extended European Search Report on corresponding European Patent Application No. 19850901.0 dated May 30, 2022 (15 pages).
Goldenberg, D. et al., "The emergence of trophoblast cell-surface antigen 2 (TROP-2) as a novel cancer target", Oncotarget, vol. No. 9, Issue No. 48, 2018, pp. 28989-29006.
Ogitani, Y. et al., "DS-8201a, A Novel HER2-Targeting ADC with a Novel DNA Topoisomerase I Inhibitor, Demonstrates a Promising Antitumor Efficacy with Differentiation from T-DM1", Clinical Cancer Research, vol. No. 22, Issue No. 20, Oct. 15, 2016, pp. 5097-5108.
Okajima, D. et al., "Datopotamab Deruxtecan, a Novel TROP2-directed Antibody-drug Conjugate, Demonstrates Potent Antitumor Activity by Efficient Drug Delivery to Tumor Cells", Molecular Cancer Therapeutics, vol. No. 20, Issue No. 12, Dec. 2021, pp. 2329-2340.
Raji, R. et al., "Uterine and ovarian carcinosarcomas overexpressing Trop-2 are sensitive to hRS7, a humanized anti-Trop-2 antibody", Journal of Experimental & Clinical Cancer Research, vol. No. 30, Issue No. 106, 2011, 7 pages.
Rapaport, F. et al., "Comprehensive evaluation of differential gene expression analysis methods for RNA-seq data", Genome Biology, vol. No. 14, Issue No. R95, 2013, 13 pages.
Shvartsur, A. et al., "Trop2 and its overexpression in cancers; regulation and clinical/therapeutic implications", Genes & Cancer, vol. No. 6, Issue Nos. 3-4, Mar. 2015, pp. 84-105.

(Continued)

*Primary Examiner* — Hong Sang
(74) *Attorney, Agent, or Firm* — Foley & Lardner LLP

(57) ABSTRACT

A method for identifying a subject to whom a medicament containing an anti-hTROP2 antibody is to be given, wherein the subject is a human patient suffering from a cancer, comprising: obtaining a biological sample from the human patient diagnosed as suffering from a cancer; evaluating an amount of expression of the hTROP2 gene at mRNA level in the biological sample; evaluating an amount of expression of the SLFN11 gene at mRNA level in the biological sample, wherein the biological sample is one that is determined to have a high amount of expression of the hTROP2 gene; and identifying the human patient who provided the biological sample, wherein the biological sample is one that is determined to have a high amount of expression of the SLFN11 gene, as a subject to whom a medicament containing an anti-hTROP2 antibody is to be given.

20 Claims, 7 Drawing Sheets

Specification includes a Sequence Listing.

(56) References Cited

OTHER PUBLICATIONS

Tang, S.-W. et al., "SLFN11 is a Transcriptional Target of EWS-FLI1 and a Determinant of Drug Response in Ewing Sarcoma", Clinical Cancer Research, vol. No. 21, Issue No. 18, Sep. 15, 2015, pp. 4184-4193.

Tian, Li et al., "Schlafen-11 sensitizes colorectal carcinoma cells to irinotecan", Anti-Cancer Drugs, vol. No. 25, Issue No. 10, 2014, pp. 1175-1181.

Kang et al., "Activity of MM-398 Nanoliposomal Irinotecan (nal-IRI), in Ewing's Family Tumour Xenografts is Associated with High Exposure of Tumour to Drug and High SLFN11 Expression," Clin Cancer Res vol. 21, Issue 5, 2015, pp. 1139-1150.

Liu et al., "Advances in the Treatment of Relapsed Small Cell Lung Cancer" Chinese Journal of Lung Cancer, vol. 20, No. 3, 2017, pp. 192-198.

Office Action and Search Report issued in corresponding Chinese Patent Application No. 201980055378.2, dated Aug. 16, 2023.

International Searching Authority, "International Search Report," issued in connection with International Patent Application No. PCT/JP2019/032773, dated Nov. 19, 2019.

International Searching Authority, "Written Opinion," issued in connection with International Patent Application No. PCT/JP2019/032773, dated Nov. 19, 2019.

Alley et al., "Antibody-drug conjugates: targeted drug delivery for cancer," Current Opinion in Chemical Biology, vol. 14, 2010, pp. 529-537.

Barretina et al., "The Cancer Cell Line Encyclopedia enables predictive modelling of anticancer drug sensitivity," Nature, vol. 483, No. 7391, Mar. 28, 2012, pp. 603-607.

Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," Journal of Clinical Oncology, vol. 29, No. 4, Feb. 1, 2011, pp. 398-405.

Damle, Nitin K., "Tumour-targeted chemotherapy with immunoconjugates of calicheamicin," Expert Opin. Biol. Ther., vol. 4, No. 9, 2004, pp. 1445-1452.

Doi et al., "Safety, pharmacokinetics, and antitumour activity of trastuzumab deruxtecan (DS-8201), a HER2-targeting antibody—drug conjugate, in patients with advanced breast and gastric or gastro-oesophageal tumours: a phase 1 dose-escalation study," The Lancet Oncology, vol. 18, Issue 11, Nov. 1, 2017, pp. 1512-1522.

Ducry et al., "Antibody—Drug Conjugates: Linking Cytotoxic Payloads to Monoclonal Antibodies," Bioconjugate Chem, vol. 21, 2010, pp. 5-13.

Duffy et al., "Companion biomarkers: paving the pathway to personalized treatment for cancer," Clinical Chemistry, vol. 59, No. 10, Oct. 1, 2013, pp. 1447-1456.

Fong et al., "High expression of TROP2 correlates with poor prognosis in pancreatic cancer," British Journal of Cancer, vol. 99, No. 8, Oct. 21, 2008, pp. 1290-1295.

Fong et al., "TROP2: a novel prognostic marker in squamous cell carcinoma of the oral cavity," Modern Pathology, vol. 21, 2008, pp. 186-191.

Goldenberg et al., "Trop-2 is a novel target for solid cancer therapy with sacituzumab govitecan (IMMU-132), an antibody-drug conjugate (ADC)," Oncotarget, vol. 6, No. 26, Sep. 8, 2015, pp. 22496-22512.

Gray et al., "Therapy of Small Cell Lung Cancer (SCLC) with a Topoisomerase-I—inhibiting Antibody—Drug Conjugate (ADC) Targeting Trop-2, Sacituzumab Govitecan," Clinical Cancer Research, vol. 23, No. 19, Oct. 1, 2017, pp. 5711-5719.

Muhlmann et al., "TROP2 expression as prognostic marker for gastric carcinoma," Journal of Clinical Pathology., vol. 62, No. 2, Feb. 2009, pp. 152-158.

Murai et al., "SLFN11 Blocks Stressed Replication Forks Independently of ATR," Molecular Cell, vol. 69, Issue 3, Feb. 1, 2018, pp. 371-384.

Ning et al., "TROP2 expression and its correlation with tumor proliferation and angiogenesis in human gliomas," Neurogical Sciences, vol. 34, 2013, pp. 1745-1750.

Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.

Ogitani et al., "DS-8201a, A Novel HER2-Targeting ADC with a Novel DNA Topoisomerase I Inhibitor, Demonstrates a Promising Antitumor Efficacy with Differentiation from T-DM1," Clinical Cancer Research, vol. 22, No. 20, Oct. 15, 2016, pp. 5097-5108.

Ohmachi et al., "Clinical Significance of TROP2 Expression in Colorectal Cancer," Clinical Cancer Research, vol. 12, No. 10, May 15, 2006, pp. 3057-3063.

Pietanza et al., "Randomized, Double-Blind, Phase II Study of Temozolomide in Combination With Either Veliparib or Placebo in Patients With Relapsed-Sensitive or Refractory Small-Cell Lung Cancer," Journal of Clinical Oncology, vol. 36, No. 23, pp. 2386-2394, 2018.

Senter et al., "The discovery and development of brentuximab vedotin for use in relapsed Hodgkin lymphoma and systemic anaplastic large cell lymphoma," Nature Biotechnology, vol. 30, No. 7, Jul. 2012, pp. 631-637.

Starodub et al., "First-in-Human Trial of a Novel Anti-Trop-2 Antibody-SN-38 Conjugate, Sacituzumab Govitecan, for the Treatment of Diverse Metastatic Solid Tumors," Clinical Cancer Research, vol. 21, No. 17, Sep. 1, 2015, pp. 3870-3878.

Takegawa et al., "DS-8201a, a new HER2-targeting antibody-drug conjugate incorporating a novel DNA topoisomerase I inhibitor, overcomes HER2-positive gastric cancer T-DM1 resistance," International Journey of Cancer, vol. 141, 2017, pp. 1682-1689.

Van Den Borg et al., "Novel targeted strategies to overcome resistance in small-cell lung cancer: focus on PARP inhibitors and rovalpituzumab tesirine," Expert Review of Anticancer Therapy, vol. 19, No. 6, 2019, pp. 461-471.

Wang et al., "Identification of Trop-2 as an oncogene and an attractive therapeutic target in colon cancers," Molecular Cancer Therapeutics, vol. 7, No. 2, Feb. 2008, pp. 280-285.

Zoppoli et al., "Putative DNA/RNA helicase Schlafen-11 (SLFN11) sensitizes cancer cells to DNA-damaging agents," Proc Natl Acad Sci USA, vol. 109, No. 37, Sep. 11, 2012, pp. 15030-15035.

* cited by examiner

[Figure 1]

SEQ ID NO: 1: Amino acid sequence of the heavy chain of a humanized anti-hTROP2 antibody MKHLWFFLLLVAAPRWVLSQVQLVQSGAEVKKPGASVKVSCKASGYTFTTAGMQWVR
QAPGQGLEWMGWINTHSGVPKYAEDFKGRVTISADTSTSTAYLQLSSLKSEDTAVYY
CARSGFGSSYWYFDVWGQGTLVTVSSASTKGPSVFPLAPSSKSTSGGTAALGCLVKD
YFPEPVTVSWNSGALTSGVHTFPAVLQSSGLYSLSSVVTVPSSSLGTQTYICNVNHK
PSNTKVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALH
NHYTQKSLSLSPGK Signal sequence (1-19), Variable region (20-140), Constant region (141-470)

[Figure 2]

SEQ ID NO: 2: Amino acid sequence of the light chain of a humanized anti-hTROP2 antibody MVLQTQVFISLLLWISGAYGDIQMTQSPSSLSASVGDRVTITCKASQDVSTAVAWYQ
QKPGKAPKLLIYSASYRYTGVPSRFSGSGSGTDFTLTISSLQPEDFAVYYCQQHYIT
PLTFGQGTKLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKS
FNRGEC Signal sequence (1-20), Variable region (21-129), Constant region (130-234)

[Figure 3]

SEQ ID NO: 3: CDRH1 sequence of the heavy chain of a humanized anti-hTROP2 antibody

TAGMQ

SEQ ID NO: 4: CDRH2 sequence of the heavy chain of a humanized anti-hTROP2 antibody

WINTHSGVPKYAEDFKG

SEQ ID NO: 5: CDRH3 sequence of the heavy chain of a humanized anti-hTROP2 antibody

SGFGSSYWYFDV

SEQ ID NO: 6: CDRL1 sequence of the light chain of a humanized anti-hTROP2 antibody

KASQDVSTAVA

SEQ ID NO: 7: CDRL2 sequence of the light chain of a humanized anti-hTROP2 antibody

SASYRYT

SEQ ID NO: 8: CDRL3 sequence of the light chain of a humanized anti-hTROP2 antibody

QQHYITPLT

[Figure 4]
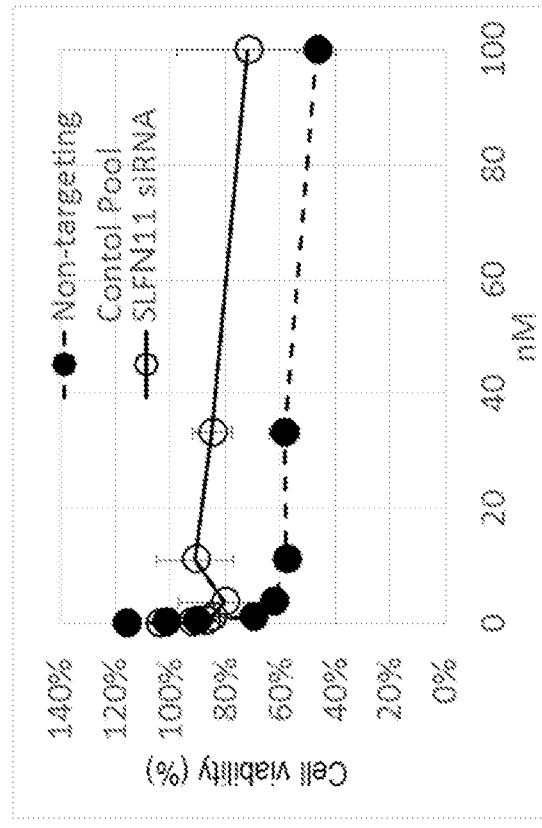
Addition of compound (1)
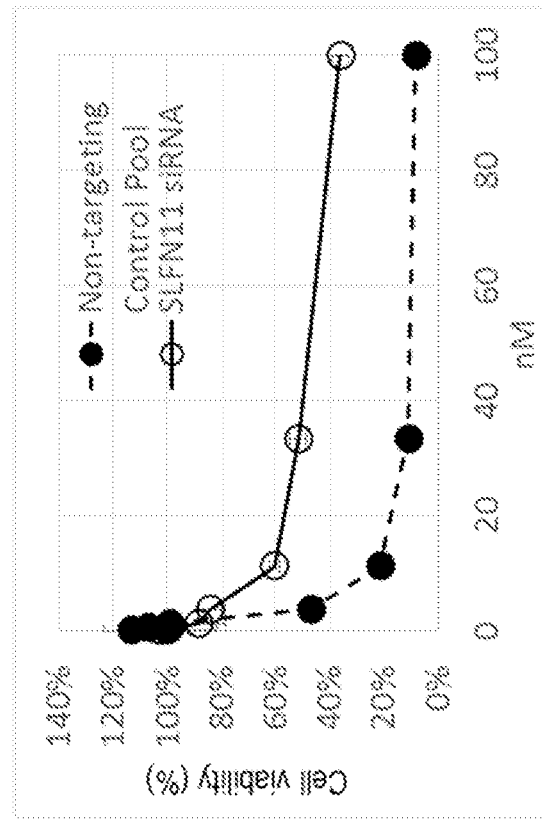
Addition of antibody-drug conjugate (1)

[Figure 5]
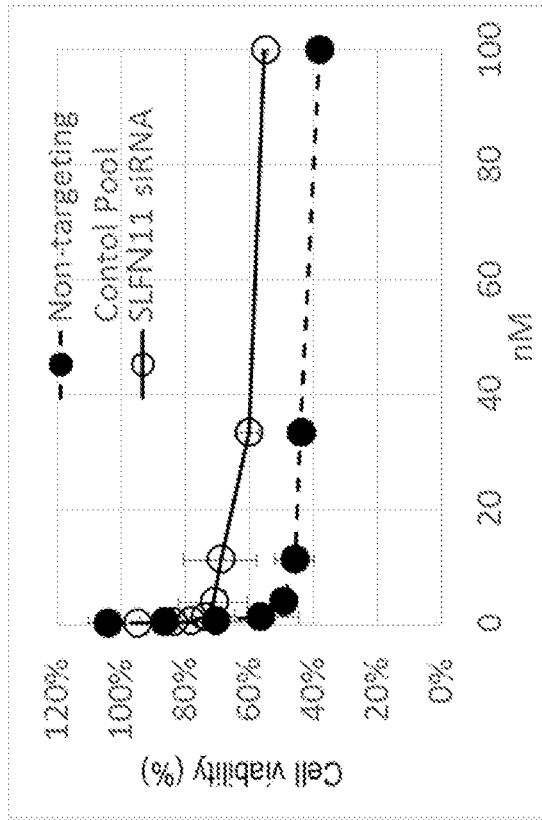
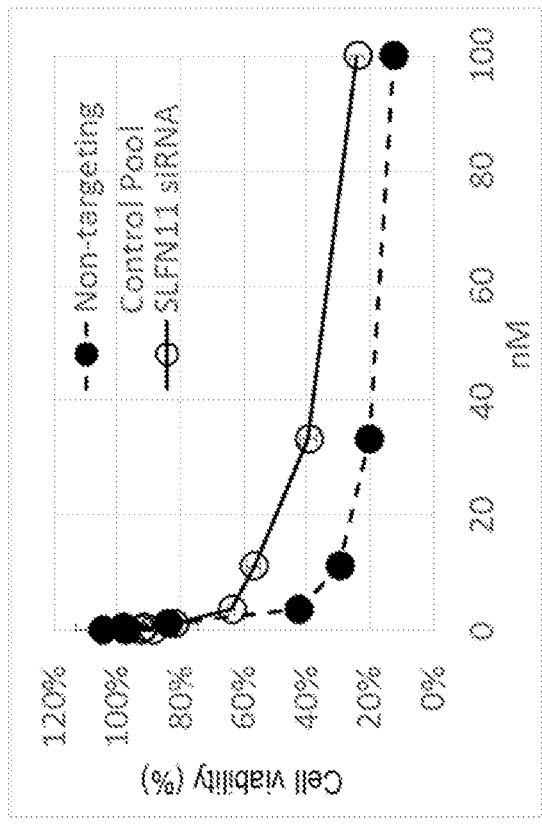

[Figure 6]
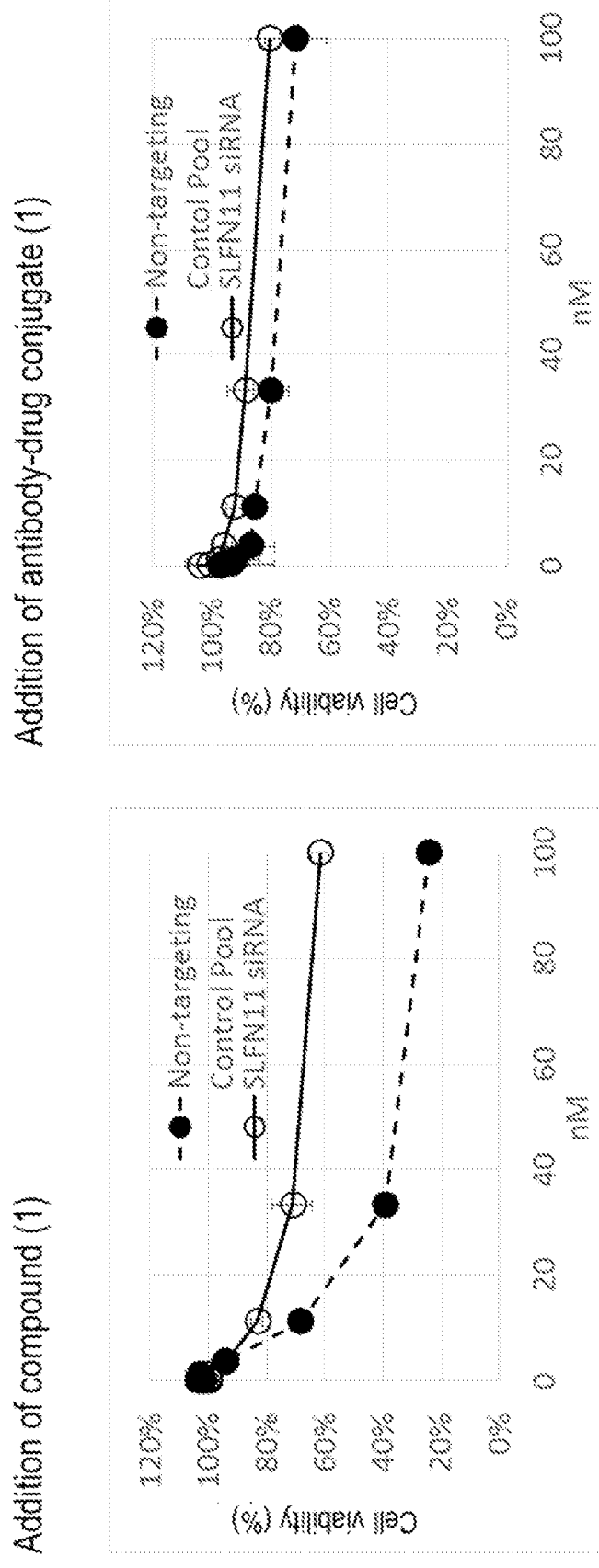

[Figure 7]
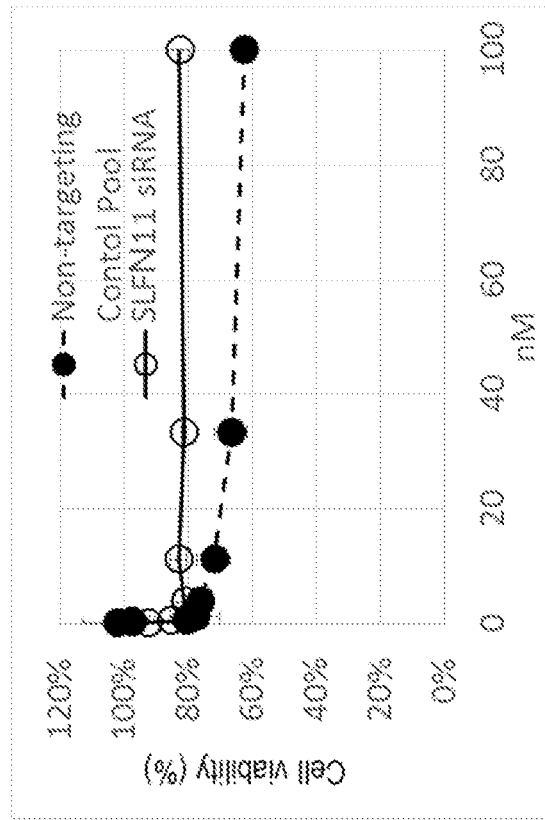
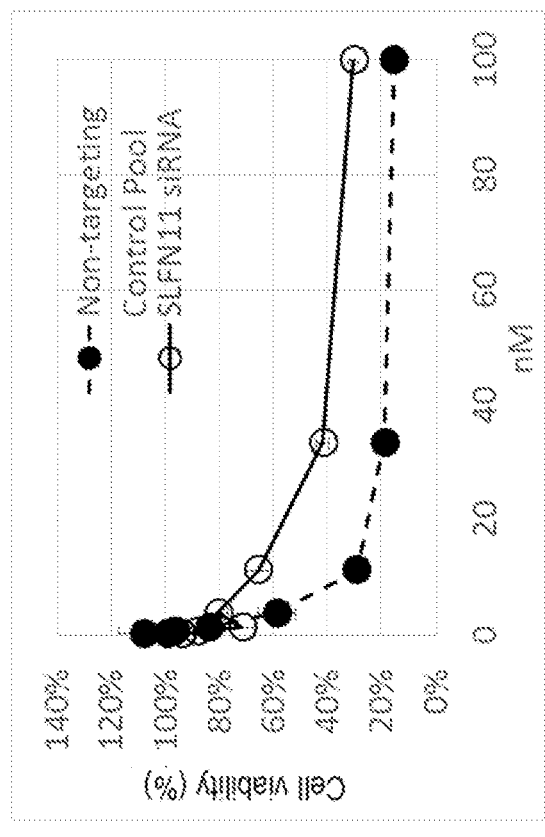

[Figure 8]
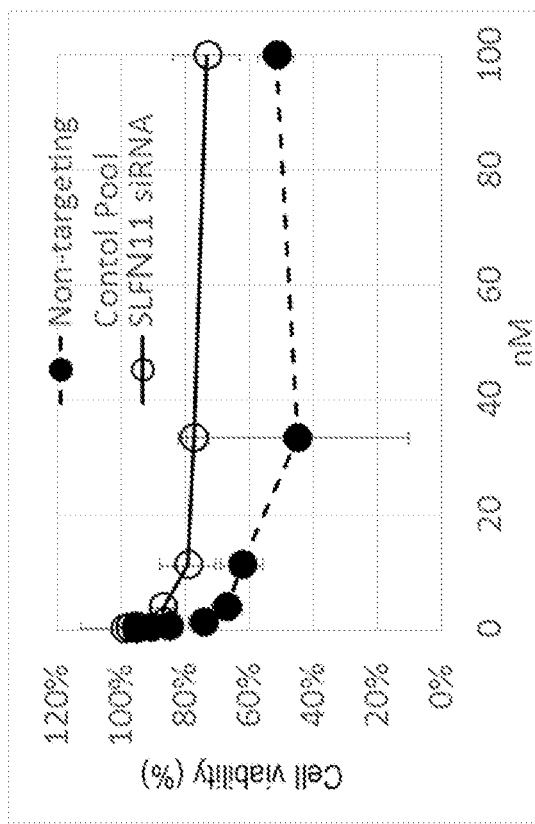
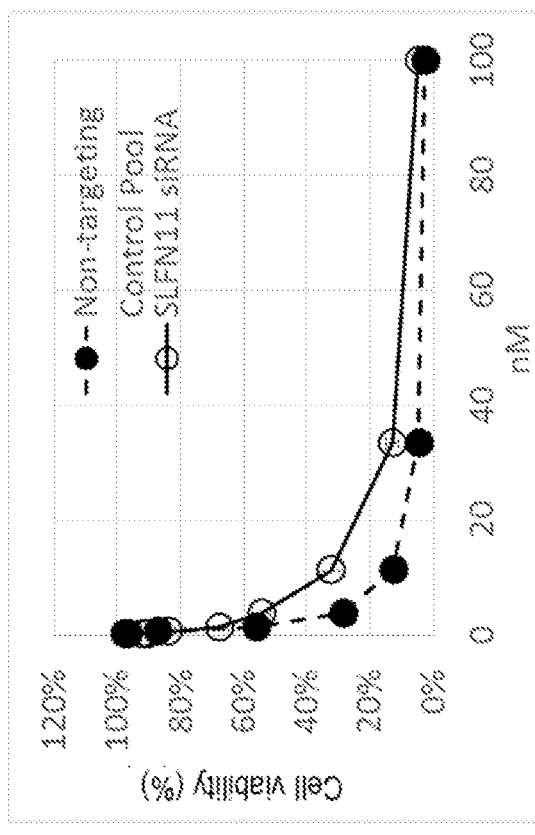

```
                        SEQUENCE LISTING

<160> NUMBER OF SEQ ID NOS: 8

<210> SEQ ID NO 1
<211> LENGTH: 470
<212> TYPE: PRT
<213> ORGANISM: Artificial
<220> FEATURE:
<223> OTHER INFORMATION: amino acid sequence of heavy chain of a
      humanized anti-hTROP2 antibody

<400> SEQUENCE: 1

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Ala Gly Met Gln Trp Val Arg Gln Ala Pro Gly Gln Gly Leu
    50                  55                  60

Glu Trp Met Gly Trp Ile Asn Thr His Ser Gly Val Pro Lys Tyr Ala
65                  70                  75                  80

Glu Asp Phe Lys Gly Arg Val Thr Ile Ser Ala Asp Thr Ser Thr Ser
                85                  90                  95

Thr Ala Tyr Leu Gln Leu Ser Ser Leu Lys Ser Glu Asp Thr Ala Val
            100                 105                 110

Tyr Tyr Cys Ala Arg Ser Gly Phe Gly Ser Ser Tyr Trp Tyr Phe Asp
        115                 120                 125

Val Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240
```

Lys Ser Cys Asp Lys Thr His Thr Cys Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 2
<211> LENGTH: 234
<212> TYPE: PRT
<213> ORGANISM: Artificial
<220> FEATURE:
<223> OTHER INFORMATION: amino acid sequence of light chain of a
      humanized anti-hTROP2 antibody

<400> SEQUENCE: 2

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Val Tyr Tyr Cys Gln Gln His Tyr
            100                 105                 110

Ile Thr Pro Leu Thr Phe Gly Gln Gly Thr Lys Leu Glu Ile Lys Arg
        115                 120                 125

```
Thr Val Ala Ala Pro Ser Val Phe Ile Phe Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 3
<211> LENGTH: 5
<212> TYPE: PRT
<213> ORGANISM: Artificial
<220> FEATURE:
<223> OTHER INFORMATION: amino acid sequence of CDRH1 in heavy chain of
      a humanized anti-hTROP2 antibody

<400> SEQUENCE: 3

```
Thr Ala Gly Met Gln
1               5
```

<210> SEQ ID NO 4
<211> LENGTH: 17
<212> TYPE: PRT
<213> ORGANISM: Artificial
<220> FEATURE:
<223> OTHER INFORMATION: amino acid sequence of CDRH2 in heavy chain of
      a humanized anti-hTROP2 antibody

<400> SEQUENCE: 4

```
Trp Ile Asn Thr His Ser Gly Val Pro Lys Tyr Ala Glu Asp Phe Lys
1               5                   10                  15

Gly
```

<210> SEQ ID NO 5
<211> LENGTH: 12
<212> TYPE: PRT
<213> ORGANISM: Artificial
<220> FEATURE:
<223> OTHER INFORMATION: amino acid sequence of CDRH3 in heavy chain of
      a humanized anti-hTROP2 antibody

<400> SEQUENCE: 5

```
Ser Gly Phe Gly Ser Ser Tyr Trp Tyr Phe Asp Val
1               5                   10
```

<210> SEQ ID NO 6
<211> LENGTH: 11
<212> TYPE: PRT
<213> ORGANISM: Artificial
<220> FEATURE:
<223> OTHER INFORMATION: amino acid sequence of CDRL1 in light chain of
      a humanized anti-hTROP2 antibody

<400> SEQUENCE: 6

```
Lys Ala Ser Gln Asp Val Ser Thr Ala Val Ala
1               5                   10
```

```
<210> SEQ ID NO 7
<211> LENGTH: 7
<212> TYPE: PRT
<213> ORGANISM: Artificial
<220> FEATURE:
<223> OTHER INFORMATION: amino acid sequence of CDRL2 in light chain of
      a humanized anti-hTROP2 antibody

<400> SEQUENCE: 7

Ser Ala Ser Tyr Arg Tyr Thr
1               5

<210> SEQ ID NO 8
<211> LENGTH: 9
<212> TYPE: PRT
<213> ORGANISM: Artificial
<220> FEATURE:
<223> OTHER INFORMATION: amino acid sequence of CDRL3 in light chain of
      a humanized anti-hTROP2 antibody

<400> SEQUENCE: 8

Gln Gln His Tyr Ile Thr Pro Leu Thr
1               5
```

SENSITIVITY MARKER FOR ANTIBODY-DRUG CONJUGATE

CROSS-REFERENCE TO RELATED APPLICATIONS

The present application claims priority under 37 U.S.C. § 371 to International Patent Application No. PCT/JP2019/032773, filed Aug. 22, 2019, which claims priority to and the benefit of Japanese Patent Application No. 2018-156449, filed on Aug. 23, 2018. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 122622-0132_SL.txt and is 8 kb in size.

TECHNICAL FIELD

The present invention relates to a method for identifying a subject to whom a medicament containing an antibody-drug conjugate is to be given, wherein the subject is a human patient suffering from a cancer.

BACKGROUND ART

Most anti-cancer agents are effective for certain human patients, but not for other human patients. This is based on the genetic diversity of cancers, and such differences may even be observed among cancers within the same patient. Differences in drug efficacy between patients is particularly significant in molecular-targeted anti-cancer agents. Proper testing is thus needed to determine which anti-cancer agent is effective against which patient. Without such testing, it cannot be expected that an anti-cancer agent will exert its effect sufficiently. Diagnostic methods have been established that are based on the discovery of sensitivity markers, which identify patients beforehand who are likely to have a clinical response to new anti-cancer agents, thereby accelerating the development of the agents. This makes it possible to reduce significantly the scale, period, and cost of the clinical studies. Techniques of genomics, proteomics, or molecular imaging should have allowed for rapid and highly sensitive detection of sensitivity markers. However, although various techniques related to gene profiling of cancers have become available, it does not appear to be the case that the practical application of sensitivity markers for anti-cancer agents is widely used.

Examples of the target of the molecular-targeted anti-cancer agent described above include human TROP2. Human TROP2 (Trophoblast Cell Surface Protein 2, TAC-STD2: Tumor-Associated Calcium Signal Transducer 2, GA733-1, EGP-1, M1S1; hereinafter referred to as hTROP2) is a type 1, one-transmembrane, cell membrane protein consisting of 323 amino acid residues.

Immunohistochemical analysis using clinical specimens has shown that hTROP2 is overexpressed in various epithelial cell-derived cancers, and that expression in normal tissues is limited to epithelial cells of several tissues, and the amount of expression is low in normal tissues compared to in tumor tissues (Non Patent Literatures 1 to 5). It has also been reported that expression of hTROP2 is correlated with poor prognosis in colorectal cancer (Non Patent Literature 1), gastric cancer (Non Patent Literature 2), pancreatic cancer (Non Patent Literature 3), oral cancer (Non Patent Literature 4), and glioma (Non Patent Literature 5). Furthermore, it has been reported from models using colorectal cancer cells that expression of hTROP2 is involved in scaffold-independent cell proliferation of cancer cells and tumor formation in immunodeficient mice (Non Patent Literature 6).

From such information suggesting relations with cancers, multiple anti-hTROP2 antibodies have been established to date, and their anti-tumor effects have been studied. It is disclosed that such anti-hTROP2 antibodies include an antibody that exhibits anti-tumor activity in a nu/nu mouse xenograft model as an antibody alone (Patent Literatures 1 to 4), and an antibody that exhibits anti-tumor activity as an antibody-drug conjugate (Patent Literatures 5 to 7). However, the strength of activity and the scope of application of these are not yet sufficient, and there are unmet medical needs that could be addressed by selecting hTROP2 as a target for treatment. The reasons why existing antibodies or antibody-drug conjugates have not met medical needs include not only because they are not sufficiently effective as medicaments, but also because no suitable sensitivity markers have been found. For example, it is known that, the anti-tumor activity exhibited by an antibody-drug conjugate targeting hTROP2 in small cell lung cancer is not predicted by the amount of expression of hTROP2 alone (Non Patent Literature 7).

Antibody-drug conjugates (hereinafter, sometimes referred to "ADCs") in which a cytotoxic drug is conjugated to an antibody that binds to an antigen expressed on the surface of a cancer cell and is capable of being internalized into the cell can be expected to selectively deliver the drug to the cancer cell, accumulate the drug in the cancer cell, and kill the cancer cell. One known example of such antibody-drug conjugates is an antibody-drug conjugate including as its components an antibody and a derivative of exatecan, which is a topoisomerase I inhibitor (Patent Literatures 9 to 15, Non Patent Literatures 8 to 16). The antibody-drug conjugate described in Patent Literature 9 includes an anti-hTROP2 antibody and is capable of killing cancer cells that express hTROP2. However, similar to the existing antibodies or antibody-drug conjugates targeting hTROP2, the anti-tumor activity of the antibody-drug conjugate is not accurately predicted by the amount of expression of hTROP2 alone.

Human SLFN11 (Schlafen family member 11) is a protein consisting of 901 amino acid residues, and has been suggested to have a function of binding to replication forks in response to DNA replication stress, and inhibiting DNA replication (Non Patent Literature 17). It has also been reported that the sensitivity of cancer cell lines to DNA-damaging anti-cancer agents, including topoisomerase I inhibitors, correlates highly with the amount of mRNA expression of SLFN11 (Non Patent Literatures 18 to 19). It is also known that the combination of veliparib, a polyADP ribose polymerase (PARP) inhibitor, and rovalpituzumab tesirine (Rova-T), an anti-DLL3 antibody-drug conjugate, provides a survival benefit for patients with small cell lung cancer that highly expresses SLFN11 (Non Patent Literature 20). Furthermore, it is known that the combination of an alkylating agent, Temozolomide, and veliparib provides a survival benefit for patients with small cell lung cancer that highly expresses SLFN11 (Non Patent Literature 21). However, the relationship between the anti-tumor activity of an ADC using a topoisomerase I inhibitor, such as exatecan, and the amount of expression of SLFN11 has not yet been clarified, and the effectiveness thereof as a diagnostic agent for predicting drug efficacy is unclear.

CITATION LIST

Patent Literature

Patent Literature 1: WO 2008/144891
Patent Literature 2: WO 2011/145744
Patent Literature 3: WO 2011/155579
Patent Literature 4: WO 2013/077458
Patent Literature 5: WO 2003/074566
Patent Literature 6: WO 2011/068845
Patent Literature 7: WO 2013/068946
Patent Literature 8: U.S. Pat. No. 7,999,083
Patent Literature 9: WO 2014/057687
Patent Literature 10: WO 2014/061277
Patent Literature 11: WO 2015/098099
Patent Literature 12: WO 2015/115091
Patent Literature 13: WO 2015/146132
Patent Literature 14: WO 2015/155976
Patent Literature 15: WO 2015/155998

Non Patent Literature

Non Patent Literature 1: Ohmachi T, et al., Clin. Cancer Res., 12(10), 3057-3063 (2006)
Non Patent Literature 2: Muhlmann G, et al., J. Clin. Pathol., 62(2), 152-158 (2009)
Non Patent Literature 3: Fong D, et al., Br. J. Cancer, 99(8), 1290-1295 (2008)
Non Patent Literature 4: Fong D, et al., Mod. Pathol., 21(2), 186-191 (2008)
Non Patent Literature 5: Ning S, et al., Neurol. Sci., 34(10), 1745-1750 (2013)
Non Patent Literature 6: Wang J, et al., Mol. Cancer Ther., 7(2), 280-285 (2008)
Non Patent Literature 7: Gray J. E., et al. Clin. Cancer Res. 23(19), 5711-5719 (2017)
Non Patent Literature 8: Ducry, L., et al., Bioconjugate Chem. (2010) 21, 5-13
Non Patent Literature 9: Alley, S. C., et al., Current Opinion in Chemical Biology (2010) 14, 529-537
Non Patent Literature 10: Damle N. K. Expert Opin. Biol. Ther. (2004) 4, 1445-1452
Non Patent Literature 11: Senter P. D., et al., Nature Biotechnology (2012) 30, 631-637
Non Patent Literature 12: Howard A. et al., J Clin Oncol 29: 398-405
Non Patent Literature 13: Ogitani Y. et al., Clinical Cancer Research (2016) 22(20), 5097-5108
Non Patent Literature 14: Ogitani Y. et al., Cancer Science (2016) 107, 1039-1046
Non Patent Literature 15: Doi T, et al., Lancet Oncol 2017; 18: 1512-22
Non Patent Literature 16: Takegawa N, et al., Int. J. Cancer: 141, 1682-1689 (2017)
Non Patent Literature 17: Murai J, et al., Mol. Cell 69(3), 371-384 (2018)
Non Patent Literature 18: Zoppoli G, et al., Proc. Natl. Acad. Sci. U.S.A., 109(37):15030-15035 (2012)
Non Patent Literature 19: Barretina J, et al., Nature 483 (7391), 603-607 (2012)
Non Patent Literature 20: Van Den Borg R, et al., Expert Rev. Anticancer Ther., 19 (6), 461-471 (2019)
Non Patent Literature 21: Pietanza M C, et al., J, Clin. Oncol. 36 (23), 2386-2394 (2018)

SUMMARY OF INVENTION

Technical Problem

The present invention relates to a method for identifying a subject to whom a medicament containing an anti-hTROP2 antibody is to be given, wherein the subject is a human patient suffering from a cancer, using gene expression at mRNA level as an indicator.

Solution to Problem

The present inventors have found that the amount of expression of the hTROP2 gene and the SLFN11 gene at mRNA level in combination enables more accurate identification of a subject to whom a medicament containing an anti-hTROP2 antibody is to be given, and completed the present invention.

That is, the present invention includes each of the following items, but is not limited thereto.

[1] A method for identifying a subject to whom a medicament containing an anti-hTROP2 antibody is to be given, wherein the subject is a human patient suffering from a cancer, the method comprising:
  1) obtaining a biological sample from the human patient diagnosed as suffering from a cancer;
  2) evaluating an amount of expression of the hTROP2 gene at mRNA level in the biological sample;
  3) evaluating an amount of expression of the SLFN11 gene at mRNA level in the biological sample, wherein the biological sample is one that is determined to have a high amount of expression of the hTROP2 gene; and
  4) identifying the human patient who provided the biological sample, wherein the biological sample is one that is determined to have a high amount of expression of the SLFN11 gene, as a subject to whom a medicament containing an anti-hTROP2 antibody is to be given.

[2] A method for identifying a subject to whom a medicament containing an anti-hTROP2 antibody is to be given, wherein the subject is a human patient suffering from a cancer, the method comprising:
  1) obtaining a biological sample from the human patient diagnosed as suffering from a cancer;
  2) evaluating an amount of expression of the hTROP2 gene and the SLFN11 gene at mRNA level in the biological sample; and
  3) identifying the human patient who provided the biological sample, wherein the biological sample is one that is determined to have a high amount of expression of the hTROP2 gene and the SLFN11 gene, as a subject to whom a medicament containing an anti-hTROP2 antibody is to be given.

[3] The method according to [1] or [2], wherein a $\log_2$[RPKM+1] value is measured by RNA sequencing from the biological sample obtained from the human patient diagnosed as suffering from a cancer, and the biological sample is determined to have a high amount of expression of the hTROP2 gene and/or the SLFN11 gene at mRNA level when the $\log_2$[RPKM+1] value exceeds a specific value.

[4] The method according to [3], wherein the biological sample is determined to have a high amount of expression of the hTROP2 gene at mRNA level when the $\log_2$[RPKM+1] value exceeds any one selected from the group consisting of 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, and 9.0.

[5] The method according to [3] or [4], wherein the biological sample is determined to have a high amount of expression of the hTROP2 gene at mRNA level when the $\log_2[\text{RPKM}+1]$ value exceeds any one selected from the group consisting of 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0.

[6] The method according to any one of [3] to [5], wherein the biological sample is determined to have a high amount of expression of the hTROP2 gene at mRNA level when the $\log_2[\text{RPKM}+1]$ value exceeds any one selected from the group consisting of 6.5, 6.6, 6.7, 6.8, 6.9, 7.0, 7.1, 7.2, 7.3, 7.4, 7.5, 7.6, 7.7, 7.8, 7.9, and 8.0.

[7] The method according to any one of [3] to [6], wherein the biological sample is determined to have a high amount of expression of the hTROP2 gene at mRNA level when the $\log_2[\text{RPKM}+1]$ value exceeds any one selected from the group consisting of 7.0, 7.1, 7.2, 7.3, 7.4, 7.5, 7.6, 7.7, 7.8, 7.9, and 8.0.

[8] The method according to any one of [3] to [7], wherein the biological sample is determined to have a high amount of expression of the hTROP2 gene at mRNA level when the $\log_2[\text{RPKM}+1]$ value exceeds any one selected from the group consisting of 7.5, 7.6, 7.7, 7.8, 7.9, and 8.0.

[9] The method according to any one of [3] to [7], wherein the biological sample is determined to have a high amount of expression of the hTROP2 gene at mRNA level when the $\log_2[\text{RPKM}+1]$ value exceeds any one selected from the group consisting of 7.0, 7.5, and 8.0.

[10] The method according to [9], wherein the biological sample is determined to have a high amount of expression of the hTROP2 gene at mRNA level when the $\log_2[\text{RPKM}+1]$ value exceeds 7.0.

[11] The method according to [9], wherein the biological sample is determined to have a high amount of expression of the hTROP2 gene at mRNA level when the $\log_2[\text{RPKM}+1]$ value exceeds 7.5.

[12] The method according to [9], wherein the biological sample is determined to have a high amount of expression of the hTROP2 gene at mRNA level when the $\log_2[\text{RPKM}+1]$ value exceeds 8.0.

[13] The method according to any one of [3] to [12], wherein the biological sample is determined to have a high amount of expression of the SLFN11 gene at mRNA level when the $\log_2[\text{RPKM}+1]$ value exceeds any one selected from the group consisting of 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0.

[14] The method according to any one of [3] to [13], wherein the biological sample is determined to have a high amount of expression of the SLFN11 gene at mRNA level when the $\log_2[\text{RPKM}+1]$ value exceeds any one selected from the group consisting of 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0.

[15] The method according to any one of [3] to [14], wherein the biological sample is determined to have a high amount of expression of the SLFN11 gene at mRNA level when the $\log_2[\text{RPKM}+1]$ value exceeds any one selected from the group consisting of 2.0, 2.1, 2.2, 2.3, 2.4, 2.5, 2.6, 2.7, 2.8, 2.9, and 3.0.

[16] The method according to any one of [3] to [14], wherein the biological sample is determined to have a high amount of expression of the SLFN11 gene at mRNA level when the $\log_2[\text{RPKM}+1]$ value exceeds any one selected from the group consisting of 1.0, 2.0, and 3.0.

[17] The method according to [16], wherein the biological sample is determined to have a high amount of expression of the SLFN11 gene at mRNA level when the $\log_2[\text{RPKM}+1]$ value exceeds 1.0.

[18] The method according to [16], wherein the biological sample is determined to have a high amount of expression of the SLFN11 gene at mRNA level when the $\log_2[\text{RPKM}+1]$ value exceeds 2.0.

[19] The method according to [16], wherein the biological sample is determined to have a high amount of expression of the SLFN11 gene at mRNA level when the $\log_2[\text{RPKM}+1]$ value exceeds 3.0.

[20] The method according to [1] or [2], wherein a $\log_2[\text{FPKM}+1]$ value is measured by RNA sequencing from the biological sample obtained from the human patient diagnosed as suffering from a cancer, and the biological sample is determined to have a high amount of expression of the hTROP2 gene and/or the SLFN11 gene at mRNA level when the $\log_2[\text{FPKM}+1]$ value exceeds a specific value.

[21] The method according to [20], wherein the biological sample is determined to have a high amount of expression of the hTROP2 gene at mRNA level when the $\log_2[\text{FPKM}+1]$ value exceeds any one selected from the group consisting of 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0.

[22] The method according to [20] or [21], wherein the biological sample is determined to have a high amount of expression of the hTROP2 gene at mRNA level when the $\log_2[\text{FPKM}+1]$ value exceeds any one selected from the group consisting of 6.0, 6.1, 6.2, 6.3, 6.4, 6.5, 6.6, 6.7, 6.8, 6.9, and 7.0.

[23] The method according to any one of [20] to [22], wherein the biological sample is determined to have a high amount of expression of the hTROP2 gene at mRNA level when the $\log_2[\text{FPKM}+1]$ value exceeds 6.0 or 7.0.

[24] The method according to [23], wherein the biological sample is determined to have a high amount of expression of the hTROP2 gene at mRNA level when the $\log_2[\text{FPKM}+1]$ value exceeds 6.0.

[25] The method according to [23], wherein the biological sample is determined to have a high amount of expression of the hTROP2 gene at mRNA level when the $\log_2[\text{FPKM}+1]$ value exceeds 7.0.

[26] The method according to any one of [20] to [25], wherein the biological sample is determined to have a high amount of expression of the SLFN11 gene at mRNA level when the $\log_2[\text{FPKM}+1]$ value exceeds any one selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0.

[27] The method according to any one of [20] to [26], wherein the biological sample is determined to have a high amount of expression of the SLFN11 gene at mRNA level when the $\log_2[\text{FPKM}+1]$ value exceeds any one selected from the group consisting of 2.0, 2.1, 2.2, 2.3, 2.4, 2.5, 2.6, 2.7, 2.8, 2.9, and 3.0.

[28] The method according to any one of [20] to [27], wherein the biological sample is determined to have a high amount of expression of the SLFN11 gene at mRNA level when the $\log_2[\text{FPKM}+1]$ value exceeds 2.0 or 3.0.

[29] The method according to [28], wherein the biological sample is determined to have a high amount of expression of the SLFN11 gene at mRNA level when the $\log_2[\text{FPKM}+1]$ value exceeds 2.0.

[30] The method according to [28], wherein the biological sample is determined to have a high amount of expression of the SLFN11 gene at mRNA level when the $\log_2[\text{FPKM}+1]$ value exceeds 3.0.

[31] The method according to [1] or [2], wherein a $\log_2[\text{MNC}+1]$ value is measured by an EdgeSeq Assay from the biological sample obtained from the human patient diagnosed as suffering from a cancer, and the biological sample is determined to have a high amount of expression of the hTROP2 gene and/or the SLFN11 gene at mRNA level when the $\log_2[\text{MNC}+1]$ value exceeds a specific value.

[32] The method according to [31], wherein the biological sample is determined to have a high amount of expression of the hTROP2 gene at mRNA level when the $\log_2[\text{MNC}+1]$ value exceeds any one selected from the group consisting of 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, and 15.0.

[33] The method according to [31] or [32], wherein the biological sample is determined to have a high amount of expression of the hTROP2 gene at mRNA level when the $\log_2[\text{MNC}+1]$ value exceeds any one selected from the group consisting of 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, and 14.0.

[34] The method according to any one of [31] to [33], wherein the biological sample is determined to have a high amount of expression of the hTROP2 gene at mRNA level when the $\log_2[\text{MNC}+1]$ value exceeds 12.0, 13.0, or 14.0.

[35] The method according to [34], wherein the biological sample is determined to have a high amount of expression of the hTROP2 gene at mRNA level when the $\log_2[\text{MNC}+1]$ value exceeds 12.0.

[36] The method according to [34], wherein the biological sample is determined to have a high amount of expression of the hTROP2 gene at mRNA level when the $\log_2[\text{MNC}+1]$ value exceeds 13.0.

[37] The method according to [34], wherein the biological sample is determined to have a high amount of expression of the hTROP2 gene at mRNA level when the $\log_2[\text{MNC}+1]$ value exceeds 14.0.

[38] The method according to any one of [31] to [37], wherein the biological sample is determined to have a high amount of expression of the SLFN11 gene at mRNA level when the $\log_2[\text{MNC}+1]$ value exceeds any one selected from the group consisting of 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, and 13.5.

[39] The method according to any one of [31] to [38], wherein the biological sample is determined to have a high amount of expression of the SLFN11 gene at mRNA level when the $\log_2[\text{MNC}+1]$ value exceeds any one selected from the group consisting of 11.5, 11.6, 11.7, 11.8, 11.9, 12.0, 12.1, 12.2, 12.3, 12.4, and 12.5.

[40] The method according to any one of [31] to [39], wherein the biological sample is determined to have a high amount of expression of the SLFN11 gene at mRNA level when the $\log_2[\text{MNC}+1]$ value exceeds any one selected from the group consisting of 11.5, 12.0, and 12.5.

[41] The method according to [40], wherein the biological sample is determined to have a high amount of expression of the SLFN11 gene at mRNA level when the $\log_2[\text{MNC}+1]$ value exceeds 11.5.

[42] The method according to [40], wherein the biological sample is determined to have a high amount of expression of the SLFN11 gene at mRNA level when the $\log_2[\text{MNC}+1]$ value exceeds 12.0.

[43] The method according to [40], wherein the biological sample is determined to have a high amount of expression of the SLFN11 gene at mRNA level when the $\log_2[\text{MNC}+1]$ value exceeds 12.5.

[44] The method according to any one of [1] to [43], wherein the biological sample includes a tumor sample.

[45] The method according to any one of [1] to [44], wherein the medicament containing an anti-hTROP2 antibody is an anti-hTROP2 antibody-drug conjugate.

[46] The method according to [45], wherein the anti-hTROP2 antibody-drug conjugate is an antibody-drug conjugate in which a drug-linker represented by the formula:

[Formula 1]

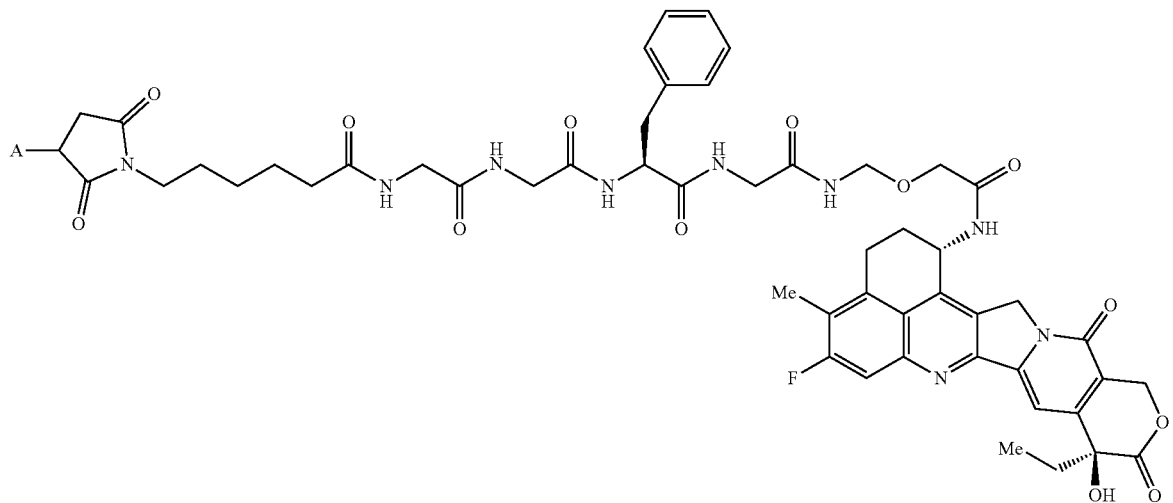

wherein A represents a connecting position to the anti-hTROP2 antibody, and the anti-hTROP2 antibody are conjugated to each other via a thioether bond.

[47] The method according to [46], wherein the anti-hTROP2 antibody is an antibody consisting of a heavy chain consisting of an amino acid sequence consisting of amino acid residues 20 to 470 of SEQ ID NO: 1 and a light chain consisting of an amino acid sequence consisting of amino acid residues 21 to 234 of SEQ ID NO: 2.

[48] The method according to [47], wherein a lysine residue at the carboxyl terminus of the heavy chain of the anti-hTROP2 antibody is deleted.

[49] The method according to any one of [46] to [48], wherein an average number of units of the drug-linker conjugated per antibody molecule ranges from 2 to 8.

[50] The method according to any one of [46] to [49], wherein an average number of units of the drug-linker conjugated per antibody molecule ranges from 3.5 to 4.5.

[51] The method according to [45], wherein the anti-hTROP2 antibody-drug conjugate is Sacituzumab Govitecan (IMMU-132).

[52] The method according to any one of [1] to [51], wherein the cancer is a lung cancer, a kidney cancer, a urothelial cancer, a colorectal cancer, a prostate cancer, polymorphic glioblastoma, an ovarian cancer, a pancreatic cancer, a breast cancer, melanoma, a liver cancer, a bladder cancer, a gastric cancer, a cervical cancer, a uterine cancer, a head and neck cancer, an esophageal cancer, a biliary tract cancer, a thyroid cancer, lymphoma, acute myeloid leukemia, acute lymphoid leukemia, and/or multiple myeloma.

The present invention further includes the following items. It should be noted that configurations or requirements of [3] to [52] can also be applied to the following inventions.

[53] A method for identifying a subject to whom a medicament containing an anti-hTROP2 antibody is to be given, wherein the subject is a human patient suffering from a cancer, the method comprising:
1) obtaining a biological sample from the human patient diagnosed as suffering from a cancer;
2) evaluating an amount of expression of the hTROP2 gene and/or the SLFN11 gene at mRNA level in the biological sample; and
3) identifying the human patient who provided the biological sample, wherein the biological sample is one that is determined to have a high amount of expression of the hTROP2 gene and/or the SLFN11 gene, as a subject to whom a medicament containing an anti-hTROP2 antibody is to be given.

[54] A method for identifying a subject to whom a medicament containing an anti-hTROP2 antibody is to be given, wherein the subject is a human patient suffering from a cancer, the method comprising:
1) obtaining a biological sample from the human patient diagnosed as suffering from a cancer;
2) evaluating an amount of expression of the hTROP2 gene at mRNA level in the biological sample; and
3) identifying the human patient who provided the biological sample, wherein the biological sample is one that is determined to have a high amount of expression of the hTROP2 gene, as a subject to whom a medicament containing an anti-hTROP2 antibody is to be given.

[55] A method for identifying a subject to whom a medicament containing an anti-hTROP2 antibody is to be given, wherein the subject is a human patient suffering from a cancer, the method comprising:
1) obtaining a biological sample from the human patient diagnosed as suffering from a cancer;
2) evaluating an amount of expression of the SLFN11 gene at mRNA level in the biological sample; and
3) identifying the human patient who provided the biological sample, wherein the biological sample is one that is determined to have a high amount of expression of the SLFN11 gene, as a subject to whom a medicament containing an anti-hTROP2 antibody is to be given.

[56] A method for identifying a subject to whom a medicament containing an anti-hTROP2 antibody is to be given, wherein the subject is a human patient suffering from a cancer, the method comprising:
1) obtaining a biological sample from the human patient diagnosed as suffering from a cancer;
2) evaluating an amount of expression of the hTROP2 gene and the SLFN11 gene at mRNA level in the biological sample; and
3) identifying the human patient who provided the biological sample, wherein the biological sample is one that is determined to have a high amount of expression of the hTROP2 gene and the SLFN11 gene, as a subject to whom a medicament containing an anti-hTROP2 antibody is to be given.

[57] A method for identifying a subject to whom a medicament containing an anti-hTROP2 antibody is to be given, wherein the subject is a human patient suffering from a cancer, the method comprising:
1) obtaining a biological sample from the human patient diagnosed as suffering from a cancer;
2) evaluating an amount of expression of the hTROP2 gene at mRNA level in the biological sample;
3) evaluating an amount of expression of the SLFN11 gene at mRNA level in the biological sample, wherein the biological sample is one that is determined to have a high amount of expression of the hTROP2 gene; and
4) identifying the human patient who provided the biological sample, wherein the biological sample is one that is determined to have a high amount of expression of the SLFN11 gene, as a subject to whom a medicament containing an anti-hTROP2 antibody is to be given.

[58] A method for identifying a subject to whom a medicament containing an anti-hTROP2 antibody is to be given, wherein the subject is a human patient suffering from a cancer, the method comprising:
1) obtaining a biological sample from the human patient diagnosed as suffering from a cancer;
2) evaluating an amount of expression of the SLFN11 gene at mRNA level in the biological sample;
3) evaluating an amount of expression of the hTROP2 gene at mRNA level in the biological sample, wherein the biological sample is one that is determined to have a high amount of expression of the SLFN11 gene; and
4) identifying the human patient who provided the biological sample, wherein the biological sample is one that is determined to have a high amount of expression of the hTROP2 gene, as a subject to whom a medicament containing an anti-hTROP2 antibody is to be given.

[59] A method for treating a cancer, comprising administering a medicament containing an anti-hTROP2 antibody, the method further comprising:
1) obtaining a biological sample from a human patient diagnosed as suffering from a cancer;
2) evaluating an amount of expression of the hTROP2 gene at mRNA level in the biological sample;
3) evaluating an amount of expression of the SLFN11 gene at mRNA level in the biological sample, wherein the biological sample is one that is determined to have a high amount of expression of the hTROP2 gene; and
4) selecting the human patient who provided the biological sample, wherein the biological sample is one that is determined to have a high amount of expression of the SLFN11 gene, as a subject to whom a medicament containing an anti-hTROP2 antibody is to be given.

[60] A method for treating a cancer, comprising administering a medicament containing an anti-hTROP2 antibody, the method further comprising:
1) obtaining a biological sample from a human patient diagnosed as suffering from a cancer;
2) evaluating an amount of expression of the hTROP2 gene and the SLFN11 gene at mRNA level in the biological sample; and
3) selecting the human patient who provided the biological sample, wherein the biological sample is one that is determined to have a high amount of expression of the hTROP2 gene and the SLFN11 gene, as a subject to whom a medicament containing an anti-hTROP2 antibody is to be given.

[61] A method for treating a cancer, comprising administering a medicament containing an anti-hTROP2 antibody, the method further comprising:
1) obtaining a biological sample from a human patient diagnosed as suffering from a cancer;
2) evaluating an amount of expression of the hTROP2 gene and/or the SLFN11 gene at mRNA level in the biological sample; and
3) selecting the human patient who provided the biological sample, wherein the biological sample is one that is determined to have a high amount of expression of the hTROP2 gene and/or the SLFN11 gene, as a subject to whom a medicament containing an anti-hTROP2 antibody is to be given.

[62] A method for treating a cancer, comprising administering a medicament containing an anti-hTROP2 antibody, the method further comprising:
1) obtaining a biological sample from a human patient diagnosed as suffering from a cancer;
2) evaluating an amount of expression of the hTROP2 gene at mRNA level in the biological sample; and
3) selecting the human patient who provided the biological sample, wherein the biological sample is one that is determined to have a high amount of expression of the hTROP2 gene, as a subject to whom a medicament containing an anti-hTROP2 antibody is to be given.

[63] A method for treating a cancer, comprising administering a medicament containing an anti-hTROP2 antibody, the method further comprising:
1) obtaining a biological sample from a human patient diagnosed as suffering from a cancer;
2) evaluating an amount of expression of the SLFN11 gene at mRNA level in the biological sample; and
3) selecting the human patient who provided the biological sample, wherein the biological sample is one that is determined to have a high amount of expression of the SLFN11 gene, as a subject to whom a medicament containing an anti-hTROP2 antibody is to be given.

[64] A method for treating a cancer, comprising administering a medicament containing an anti-hTROP2 antibody, the method further comprising:
1) obtaining a biological sample from a human patient diagnosed as suffering from a cancer;
2) evaluating an amount of expression of the hTROP2 gene and the SLFN11 gene at mRNA level in the biological sample; and
3) selecting the human patient who provided the biological sample, wherein the biological sample is one that is determined to have a high amount of expression of the hTROP2 gene and the SLFN11 gene, as a subject to whom a medicament containing an anti-hTROP2 antibody is to be given.

[65] A method for treating a cancer, comprising administering a medicament containing an anti-hTROP2 antibody, the method further comprising:
1) obtaining a biological sample from a human patient diagnosed as suffering from a cancer;
2) evaluating an amount of expression of the hTROP2 gene at mRNA level in the biological sample;
3) evaluating an amount of expression of the SLFN11 gene at mRNA level in the biological sample, wherein the biological sample is one that is determined to have a high amount of expression of the hTROP2 gene; and
4) selecting the human patient who provided the biological sample, wherein the biological sample is one that is determined to have a high amount of expression of the SLFN11 gene, as a subject to whom a medicament containing an anti-hTROP2 antibody is to be given.

[66] A method for treating a cancer, comprising administering a medicament containing an anti-hTROP2 antibody, the method further comprising:
1) obtaining a biological sample from a human patient diagnosed as suffering from a cancer;
2) evaluating an amount of expression of the SLFN11 gene at mRNA level in the biological sample;
3) evaluating an amount of expression of the hTROP2 gene at mRNA level in the biological sample, wherein the biological sample is one that is determined to have a high amount of expression of the SLFN11 gene; and
4) selecting the human patient who provided the biological sample, wherein the biological sample is one that is determined to have a high amount of expression of the hTROP2 gene, as a subject to whom a medicament containing an anti-hTROP2 antibody is to be given.

Advantageous Effects of Invention

The identification of the subject to whom a medicament containing an anti-hTROP2 antibody is to be given enables the selection of a patient in whom the medicament is expected to have an effect and the administration of the medicament to the patient.

BRIEF DESCRIPTION OF THE DRAWINGS

FIG. 1 shows an amino acid sequence of the heavy chain of a humanized anti-hTROP2 antibody (SEQ ID NO: 1).
FIG. 2 shows an amino acid sequence of the light chain of the humanized anti-hTROP2 antibody (SEQ ID NO: 2).
FIG. 3 shows a CDRH1 sequence (SEQ ID NO: 3), a CDRH2 sequence (SEQ ID NO: 4), and a CDRH3 sequence (SEQ ID NO: 5) of the heavy chain of the humanized anti-hTROP2 antibody and a CDRL1 sequence (SEQ ID NO: 6), a CDRL2 sequence (SEQ ID NO: 7), and a CDRL3 sequence (SEQ ID NO: 8) of the light chain of the humanized anti-hTROP2 antibody.
FIG. 4 is a diagram showing the cell proliferation inhibitory effects of compound (1) and antibody-drug conjugate (1) in FaDu cells upon SLFN11 knockdown.
FIG. 5 is a diagram showing the cell proliferation inhibitory effects of compound (1) and antibody-drug conjugate (1) in NCI-H1781 cells upon SLFN11 knockdown.
FIG. 6 is a diagram showing the cell proliferation inhibitory effects of compound (1) and antibody-drug conjugate (1) in Calu-3 cells upon SLFN11 knockdown.

FIG. 7 is a diagram showing the cell proliferation inhibitory effects of compound (1) and antibody-drug conjugate (1) in MDA-MB-468 cells upon SLFN11 knockdown.

FIG. 8 is a diagram showing the cell proliferation inhibitory effects of compound (1) and antibody-drug conjugate (1) in HCC38 cells upon SLFN11 knockdown.

DESCRIPTION OF EMBODIMENTS

Definition

In the present description, unless otherwise specified, when referring to numerical values, "about" means ±10% of the indicated numerical values.

In the present description, "cancer" and "tumor" are used interchangeably.

In the present description, the term "gene" includes not only DNA, but also mRNA, cDNA, and cRNA thereof.

In the present description, the term "polynucleotide" is used in the same sense as nucleic acids, and includes DNA, RNA, a probe, an oligonucleotide, and a primer.

In the present description, "polypeptide" and "protein" are used without distinction.

In the present description, "cells" include cells in an individual animal, and cultured cells.

In the present description, "hTROP2" means a human protein encoded by a gene identified by the accession number of NM_002353 (NCBI), and an allelic variant thereof, and includes a protein identified by NP_002344 (NCBI).

In the present description, "SLFN11" means a human protein encoded by a gene identified by the accession number of NM_152270 (NCBI), and an allelic variant thereof, and includes a protein identified by NP_689483 (NCBI).

In the present description, "antigen-binding fragment of an antibody" means a partial fragment of an antibody having a binding activity to an antigen, and includes Fab, F(ab')2, Fv, scFv, a diabody, a linear antibody, a multispecific antibody formed from antibody fragments, and the like. Fab', a monovalent fragment of a variable region of an antibody, obtained by treating F(ab')2 under reducing conditions, is also included in the antigen-binding fragment of an antibody. However, the antigen-binding fragment of an antibody is not limited to these molecules, as long as the fragment has a binding ability to an antigen. The antigen-binding fragment also includes not only a fragment obtained by treating a full-length molecule of an antibody protein with an appropriate enzyme, but also a protein produced in an appropriate host cell using a genetically engineered antibody gene.

In the present description, "CDR" means a complementarity determining region (CDR). It is known that each of the heavy and light chains of an antibody molecule has three CDRs. CDRs are also referred to as hypervariable regions (hypervariable domains), and are present within the variable regions of the heavy and light chains of the antibody. CDRs are sites where the mutability of the primary structure is particularly high, and are separated into three parts in each of the heavy and light chains in the primary structure of the polypeptide chain. In the present description, for CDRs of an antibody, the CDRs of the heavy chain are indicated as CDRH1, CDRH2, CDRH3 from the amino terminal side of the heavy chain amino acid sequence, and the CDRs of the light chain are indicated as CDRL1, CDRL2, CDRL3 from the amino terminal side of the light chain amino acid sequence. These sites are close to each other in the conformation of the antibody, and determine the specificity for the antigen to which the antibody binds.

In the present description, "response" to a treatment means that the tumor being treated shows (a) delay in proliferation, (b) cessation of proliferation, or (c) regression.

Anti-hTROP2 Antibody

The antibody to hTROP2 used in the present invention can be obtained, using methods normally practiced in the art, by immunizing an animal with hTROP2 or any polypeptide selected from the amino acid sequence of hTROP2, and collecting and purifying the antibody produced in the animal body. The biological species of TROP2 serving as an antigen is not limited to humans, and TROP2 derived from non-human animals such as mice or rats can also be used to immunize animals. In this case, an antibody that is to be applied to human disease can be selected by testing the cross reactivity of the obtained antibody that binds to heterologous TROP2 with hTROP2.

A monoclonal antibody can also be obtained by establishing a hybridoma by fusing an antibody-producing cell producing an antibody to hTROP2 with a myeloma cell, according to known methods (e.g., Kohler and Milstein, Nature (1975) 256, p. 495-497; Kennet, R. ed., Monoclonal Antibodies, p. 365-367, Plenum Press, N. Y. (1980)).

Note that hTROP2 serving as an antigen can be obtained by expressing the hTROP2 gene in a host cell by genetic procedures. Specifically, hTROP2 may be obtained by preparing a vector capable of expressing the hTROP2 gene, introducing the vector into a host cell to express the gene, and purifying the expressed TROP2. It is also possible to use the hTROP2-expressing cells obtained by the genetic procedures described above, or the cell lines expressing hTROP2, as hTROP2 proteins.

The antibody of the present invention also includes, in addition to the monoclonal antibody to hTROP2 described above, a gene recombinant antibody which is artificially modified for the purpose of decreasing heterologous antigenicity in humans, such as a chimeric antibody, a humanized antibody, or a human antibody. These antibodies can be produced using known methods.

Examples of the humanized antibody include, but are not limited to, a humanized antibody consisting of a heavy chain amino acid sequence represented by SEQ ID NO: 1 and a light chain amino acid sequence represented by SEQ ID NO: 2.

Various anti-hTROP2 antibodies, for example, described in WO 2008/144891, WO 2011/145744, WO 2011/155579, WO 2013/077458, WO 2003/074566, WO 2011/068845, WO 2013/068946, U.S. Pat. No. 7,999,083, or WO 2015/098099, can be used in the present invention.

It is known that a lysine residue at the carboxyl terminus of the heavy chain of an antibody produced in cultured mammalian cells is deleted (Tsubaki et al., Int. J. Biol. Macromol, 139-147, 2013). However, this deletion in the heavy chain sequence does not affect the antigen-binding ability and the effector function (such as complement activation or antibody-dependent cytotoxic action) of the antibody. Thus, the antibody with deletion of a lysine residue at the carboxyl terminus of the heavy chain described above can also be used in the present invention.

The anti-hTROP2 antibody used in the present invention also includes an antigen-binding fragment of the antibody. Examples of the antigen-binding fragment of the antibody include Fab, F(ab')2, Fv, a single chain Fv (scFv) obtained by linking the heavy and light chain Fv with an appropriate linker, a diabody or diabodies, a linear antibody, and a multispecific antibody formed from antibody fragments. Fab', a monovalent fragment of a variable region of an antibody, obtained by treating F(ab')2 under reducing conditions, is also included in the fragment of the antibody.

The anti-hTROP2 antibody used in the present invention also includes a modified variant of the antibody. The modified variant means an antibody obtained by chemically or biologically modifying the antibody of the present invention. Examples of the chemically modified variant include a variant having a chemical moiety bound to the amino acid skeleton, and a variant chemically modified with a N-linked or O-linked carbohydrate chain. Examples of the biologically modified variant include a variant subjected to post-translational modification (e.g., N-linked or O-linked glycosylation, N-terminal or C-terminal processing, deamidation, isomerization of aspartic acid, oxidation of methionine), and a variant in which a methionine residue is added to the N-terminus by expressing it in prokaryotic host cells. The anti-hTROP2 antibody used in the present invention also includes one that is labeled to enable detection or isolation of the anti-hTROP2 antibody or hTROP2, e.g., a modified variant with an enzyme label, a fluorescent label, or an affinity label. Such modified variants of the anti-hTROP2 antibody are useful for improving antibody stability and retention in blood, reducing antigenicity, detecting or isolating the anti-hTROP2 antibody or hTROP2, and the like.

It is also possible to enhance the antibody-dependent cytotoxic activity by modulation of the modification of a glycochain attached to the anti-hTROP2 antibody used in the present invention, for example, by glycosylation or defucosylation. Examples of the modulation techniques for modification of the glycochain of the antibody include, but are not limited to, those described in WO 1999/54342, WO 2000/61739, and WO 2002/31140. The anti-hTROP2 antibody used in the present invention also includes an antibody in which the glycochain modification is modulated.

Other Antibodies

The methods of the present invention can also be applied to a medicament containing an antibody other than the anti-hTROP2 antibody, which binds to an antigen. Examples of the antibody other than the anti-hTROP2 antibody used in the present invention include, but are not particularly limited to, an anti-HER2 antibody, an anti-HER3 antibody, an anti-B7-H3 antibody, an anti-CD3 antibody, an anti-CD30 antibody, an anti-CD33 antibody, an anti-CD37 antibody, an anti-CD56 antibody, an anti-CD98 antibody, an anti-DR5 antibody, an anti-EGFR antibody, an anti-EPHA2 antibody, an anti-FGFR2 antibody, an anti-FGFR4 antibody, an anti-FOLR1 antibody, an anti-VEGF antibody, an anti-CD20 antibody, an anti-CD22 antibody, an anti-CD70 antibody, an anti-PSMA antibody, an anti-CEA antibody, and an anti-Mesothelin antibody, an anti-A33 antibody, an anti-CanAg antibody, an anti-Cripto antibody, an anti-G250 antibody, an anti-MUC1 antibody, an anti-GPNMB antibody, an anti-Integrin antibody, an anti-Tenascin-C antibody, an anti-SLC44A4 antibody, anti-GPR20 antibody, and an anti-CDH6 antibody, preferably an anti-HER2 antibody, an anti-HER3 antibody, an anti-B7-H3 antibody, an anti-GPR20 antibody, and an anti-CDH6 antibody, more preferably an anti-HER2 antibody. Each antibody can be obtained in the same manner as the anti-hTROP2 antibody. Each antibody also has the universal properties that antibodies typically have, as does the anti-hTROP2 antibody.

In the present invention, "anti-HER2 antibody" refers to an antibody that specifically binds to HER2 (Human Epidermal Growth Factor Receptor Type 2; ErbB-2) and preferably has an activity of internalizing into HER2-expressing cells by binding to HER2. Examples of the anti-HER2 antibody include trastuzumab (U.S. Pat. No. 5,821,337) and pertuzumab (WO 01/00245), preferably trastuzumab. In the present invention, "anti-HER3 antibody" refers to an antibody that specifically binds to HER3 (Human Epidermal Growth Factor Receptor Type 3; ErbB-3) and preferably has an activity of internalizing into HER3-expressing cells by binding to HER3. Examples of the anti-HER3 antibody include patritumab (U3-1287), U1-59 (WO 2007/077028), MM-121 (seribantumab), an anti-ERBB3 antibody described in WO 2008/100624, RG-7116 (lumretuzumab) and LJM-716 (elgemtumab), and preferably patritumab and U1-59.

In the present invention, "anti-B7-H3 antibody" refers to an antibody that specifically binds to B7-H3 (B cell antigen #7 homolog 3; PD-L3; CD276) and preferably has an activity of internalizing into B7-H3-expressing cells by binding to B7-H3. Examples of the anti-B7-H3 antibody include M30-H1-L4 (WO 2014/057687).

In the present invention, "anti-GPR20 antibody" refers to an antibody that specifically binds to GPR20 (G Protein-coupled receptor 20) and preferably has an activity of internalizing into GPR20-expressing cells by binding to GPR20. Examples of the anti-GPR20 antibody include h046-H4e/L7 (WO 2018/135501).

In the present invention, "anti-CDH6 antibody" refers to an antibody that specifically binds to CDH6 (Cadherin-6) and preferably has an activity of internalizing into CDH6-expressing cells by binding to CDH6. Examples of the anti-CDH6 antibody include H01L02 (WO 2018/212136).

Antibody-Drug Conjugate (1)

The antibody-drug conjugate used in the present invention is an antibody-drug conjugate in which a drug-linker represented by the formula:

[Formula 2]

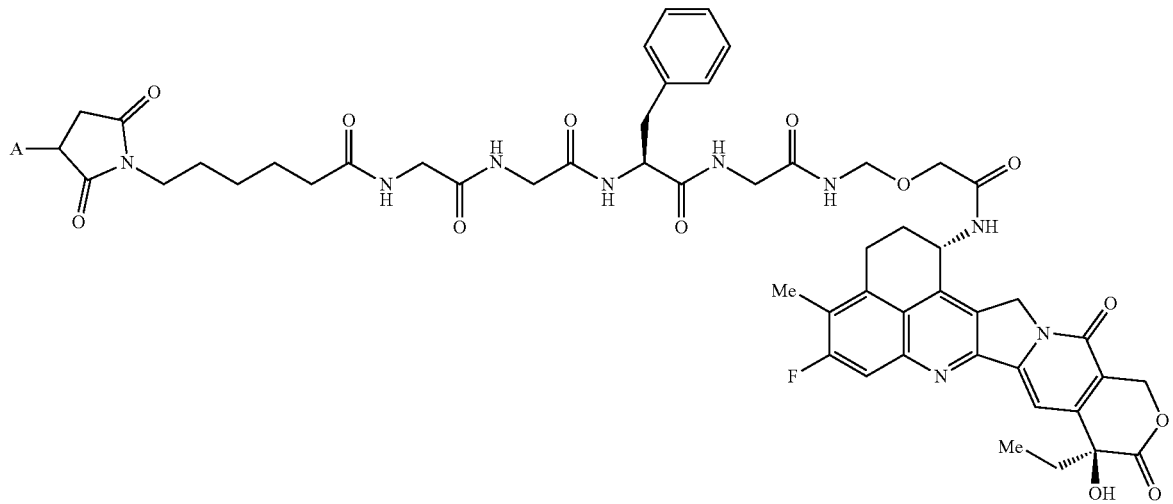

wherein A represents a connecting position to an antibody, and an antibody are conjugated to each other via a thioether bond.

In the present invention, a partial structure of the antibody-drug conjugate consisting of a linker and a drug is referred to as a "drug-linker". The drug-linker is conjugated to a thiol group (in other words, the sulfur atom of a cysteine residue) formed at an interchain disulfide bond site (between heavy chains at two locations, and between a heavy chain and a light chain at two locations).

The drug-linker of the present invention includes, as a component, exatecan (IUPAC name: (1S,9S)-1-amino-9-ethyl-5-fluoro-1,2,3,9,12,15-hexahydro-9-hydroxy-4-methyl-10H,13H-benzo[de]pyrano[3',4': 6,7]indolizino[1,2-b]quinoline-10,13-dione, (also expressed by the chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione)) which is a topoisomerase I inhibitor. Exatecan is a camptothecin derivative having an anti-tumor effect, represented by the following formula:

[Formula 3]

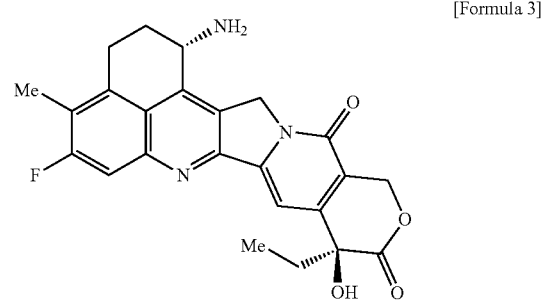 [SMILES: CC[C@@]1(O)C(=O)OCc2c1cc1n(c2=O)Cc2c-1nc1cc(F)c(C)c3c1c2[C@@H](N)CC3]

The antibody-drug conjugate used in the present invention can also be represented by the following formula:

[Formula 4]

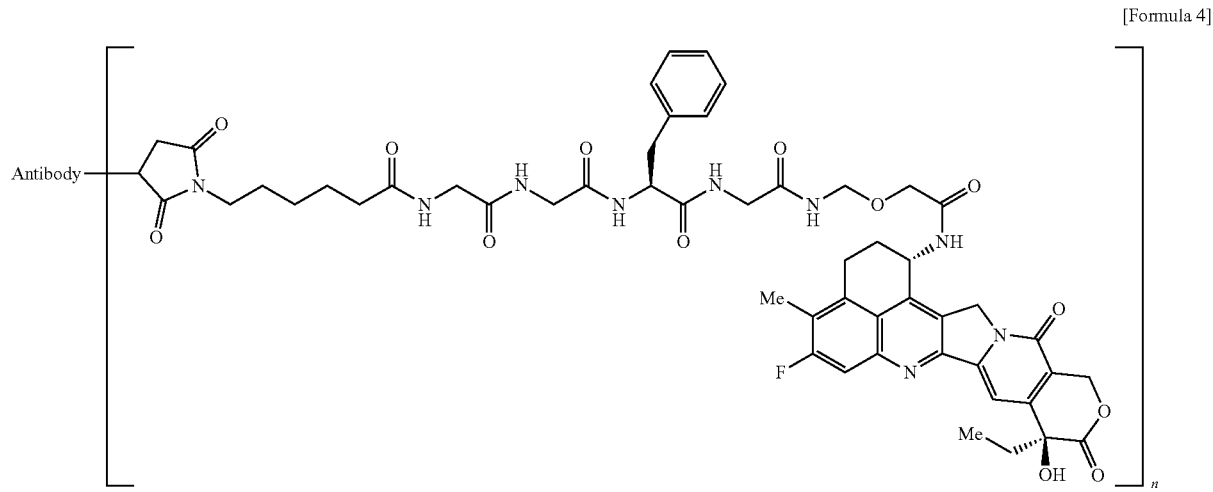

Here, the drug-linker is conjugated to an antibody via a thioether bond. The meaning of n is the same as that of the so-called Drug-to-Antibody Ratio (DAR), and indicates the average number of drug-linkers conjugated per antibody. The average number of drug-linkers conjugated per antibody of the antibody-drug conjugate used in the present invention can be adjusted in the range of 0 to 8, and preferably 2 to 8. The average number of drug-linkers conjugated when the antibody is an anti-hTROP2 antibody, is more preferably 3 to 5, still more preferably 3.5 to 4.5.

The linker portion is cleaved after the antibody-drug conjugate used in the present invention is internalized into cancer cells, and the compound represented by the following formula:

[Formula 5]

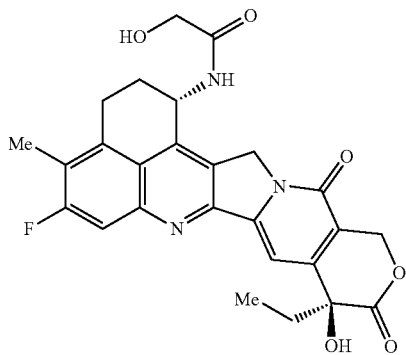

is released.

The above compound is considered to play a major role in exhibiting the anti-tumor activity of the antibody-drug conjugate used in the present invention. The compound has been confirmed to have topoisomerase I inhibitory action (Ogitani Y. et al., Clinical Cancer Research, 2016, October 15; 22(20): 5097-5108, Epub 2016 Mar. 29). The methods of the present invention can be applied without limiting the antigen recognized by the antibody to hTROP2, as long as the antibody-drug conjugate releases the above compound.

Topoisomerase I is an enzyme that transforms the high-order structure of DNA by cleaving and recombining a single strand of DNA, thereby involving the synthesis of DNA. An agent having topoisomerase I inhibitory action can thus suppress proliferation of cancer cells by inhibiting the synthesis of DNA, halting cell division in stage S (DNA synthesis stage) of the cell cycle, and inducing cell death by apoptosis.

It should be noted that the antibody-drug conjugate used in the present invention is also known to have a bystander effect (Ogitani Y. et al., Cancer Science (2016) 107, 1039-1046). This bystander effect is exerted based on the fact that, after the antibody-drug conjugate used in the present invention is internalized into a target-expressing cancer cell, the above compound also exerts an anti-tumor effect on neighboring cancer cells that have not expressed the target.

The drug-linker intermediate used in the production of the antibody-drug conjugate used in the present invention is represented by the following formula:

[Formula 6]

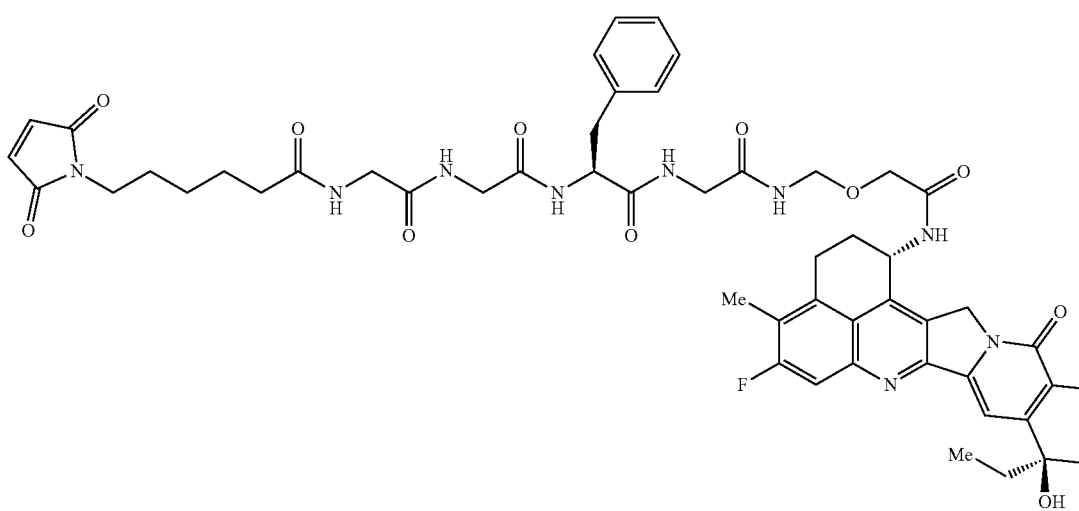

The drug-linker intermediate above can be expressed by the chemical name N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide, and can be produced by reference to the description in WO 2015/098099, or the like.

The antibody-drug conjugate used in the present invention can be produced by reacting the above-described drug-linker intermediate with an antibody having a thiol group (also referred to as a sulfhydryl group).

The antibody having a sulfhydryl group can be obtained by methods well known to those skilled in the art (Hermanson, G. T, Bioconjugate Techniques, pp. 56-136, pp. 456-493, Academic Press (1996)). For example, an antibody having a sulfhydryl group in which interchain disulfides in the antibody are partially or completely reduced can be obtained by reacting a reducing agent such as tris(2-carboxyethyl) phosphine hydrochloride (TCEP) with an antibody at 0.3 to 3 molar equivalents per interchain disulfide in the antibody in a buffer containing a chelating agent such as ethylenediaminetetraacetic acid (EDTA).

Furthermore, using 2 to 20 molar equivalents of a drug-linker intermediate per antibody having a sulfhydryl group, an antibody-drug conjugate in which 2 to 8 drugs are conjugated per antibody can be produced.

The average number of drugs conjugated per antibody molecule of the produced antibody-drug conjugate can be determined, for example, by a method of calculating which includes measuring the UV absorbance of the antibody-drug conjugate and a conjugation precursor thereof at two-wavelengths of 280 nm and 370 nm (UV method), or by a method of calculating which includes quantifying each fragment obtained by treating the antibody-drug conjugate with a reducing agent by HPLC measurement (HPLC method).

The conjugation of the antibody and the drug-linker intermediate, and the calculation of the average number of drugs conjugated per antibody molecule of the antibody-drug conjugate, can be performed with reference to the descriptions in WO 2015/098099 and WO 2017/002776, or the like.

Examples of the anti-hTROP2 antibody-drug conjugate, having the drug-linker described above, used in the present invention include antibody-drug conjugates described in WO 2015/098099. It should be noted that preferred anti-hTROP2 antibody-drug conjugates from those described in WO 2015/098099 include an antibody consisting of a heavy chain amino acid sequence containing, at a heavy chain variable region, CDRH1 (TAGMQ) consisting of an amino acid sequence represented by SEQ ID NO: 3, CDRH2 (WINTHSGVPKYAEDFKG) consisting of an amino acid sequence represented by SEQ ID NO: 4 and CDRH3 (SGFGSSYWYFDV) consisting of an amino acid sequence represented by SEQ ID NO: 5 of the sequence listing, and a light chain amino acid sequence containing, at a light chain variable region, CDRL1 (KASQDVSTAVA) consisting of an amino acid sequence represented by SEQ ID NO: 6, CDRL2 (SASYRYT) consisting of an amino acid sequence represented by SEQ ID NO: 7, and CDRL3 (QQHYITPLT) consisting of an amino acid sequence represented by SEQ ID NO: 8 of the sequence listing. More preferred anti-hTROP2 antibody-drug conjugates from those described in WO 2015/098099 include an antibody consisting of a heavy chain amino acid sequence containing a heavy chain variable region consisting of the 20th to 140th amino acid residues of an amino acid sequence represented by SEQ ID NO: 1 and a light chain amino acid sequence containing a light chain variable region consisting of the 21st to 129th amino acid residues of an amino acid sequence represented by SEQ ID NO: 2. Particularly preferred anti-hTROP2 antibody-drug conjugates from those described in WO 2015/098099 include an antibody consisting of a heavy chain amino acid sequence represented by SEQ ID NO: 1 and a light chain amino acid sequence represented by SEQ ID NO: 2.

It is known that a lysine residue at the carboxyl terminus of the heavy chain of an antibody produced in cultured mammalian cells is deleted. Thus, the antibody-drug conjugate described above also includes an antibody with a deletion of a lysine residue at the carboxyl terminus of the heavy chain.

However, the anti-hTROP2 antibody-drug conjugate used in the present invention is not limited to the conjugates including the specific drug-linker described above, as long as the antibody contained therein recognizes hTROP2. Examples of such anti-hTROP2 antibody-drug conjugates include Sacituzumab Govitecan (IMMU-132). The anti-hTROP2 antibody-drug conjugates described in WO 2003/074566, WO 2011/068845, WO 2013/068946, or U.S. Pat. No. 7,999,083 can also be used in the present invention.

Biological Sample

A biological sample collected from a subject, e.g., a subject diagnosed as suffering from a cancer, may be used as a source of RNA, and the level of gene expression at RNA level in the biological sample may be determined. The biological sample may include, for example, blood such as a whole blood or a substance derived from blood, e.g., an exosome, a tissue, a cell, and/or circulating cells from tissues. In some embodiments, the biological sample may be taken from a tumor.

An exosome is a vesicle composed of a lipid double membrane that is secreted from a cell. From their discovery in the 1980s to date, numerous studies have shown that exosomes transfer between cells and transport various molecules. Due to their morphological characteristics, exosomes include many physiologically active molecules such as nucleic acids, carbohydrates and lipids, as well as proteins. It has been also revealed that exosomes contains miRNAs and mRNAs which are transported between the cells. Thus, it is also possible to select exosomes as the biological sample to which the present invention is applied.

The biological sample may be obtained by known means, such as venipuncture, or using known tumor biopsy devices and procedures. Examples of acknowledged medical procedures that may be used by those skilled in the art to obtain a tumor sample include endoscopy, resection biopsy, incision biopsy, microneedle biopsy, punch biopsy, cutting biopsy, and skin biopsy. The biological sample should be of a size to provide sufficient RNA or to provide a slice, for measuring gene expression.

In some embodiments, the methods of the present application include a step of evaluating gene expression at mRNA level in a human subject diagnosed as suffering from a cancer who has given consent to provide an autologous tissue sample or to collect an autologous tissue sample.

The biological sample may be in any form that allows the measurement of gene expression or an amount thereof. In other words, the sample must be sufficient for RNA extraction or thin layer preparation. Accordingly, the sample may be fresh, stored using a suitable cryogenic technique, or stored using a non-cryogenic technique. For example, a standard process of manipulating a clinical biopsy sample includes immobilizing a tissue sample in formalin and embedding it in paraffin. This form of sample is usually known as a formalin-fixed paraffin-embedded (FFPE) tissue. Suitable techniques for tissue preparation for subsequent analysis are well known to those skilled in the art.

Gene Expression

In the present application, the determination or measurement of the gene expression level in the biological sample is performed using an appropriate method. Some such methods are well known in the art. For example, determination of gene expression is performed by measuring a level or an amount of RNA, e.g., mRNA, in a sample.

The primer and/or probe to be used in PCR or microarray is designed based on the 3' end of the mRNA. This is because that it is believed to result in high conservability (stability) in the course of the experimental processes of RNA isolation or cDNA synthesis. The probe may be designed based on a desired sequence to detect a transcription variant in a particular form. Examples of appropriate detection methods are shown below, but the detection methods are not limited thereto.

RNA Analysis

Examples of methods for determining the level of gene expression at mRNA level include known microarray analysis and quantitative polymerase chain reaction (PCR). In some embodiments, RNA is extracted from a cell, a tumor, or a tissue, using standard protocols. In other embodiments, RNA analysis is performed using techniques that do not require RNA isolation.

Methods for rapid and efficient extraction of eukaryotic mRNA (i.e., poly(a)RNA) from a tissue sample are well established and known to those skilled in the art. See, for example, Ausubel et al., 1997, Current Protocols of Molecular Biology, John Wiley & Sons. The tissue sample may be a fresh, frozen, or fixed and paraffin-embedded (FFPE), clinical research tumor specimen. Generally, RNA isolated from fresh or frozen tissue samples tends to be less fragmented than RNA from FFPE samples. However, FFPE samples of tumor materials are more readily available, and FFPE samples are an appropriate source of RNA for use in the methods of the present invention. For a discussion of FFPE samples as RNA sources for gene expression profiling by RT-PCR, see, for example, Clark-Langone et al., 2007, BMC Genomics 8:279. See also De Andreus et al., 1995, Biotechniques 18: 42044; and Baker et al., U.S. Patent Application Publication No. 2005/0095634.

It is common to use a commercially available kit with a vendor's instruction for RNA extraction and preparation. Examples of commercial vendors of various RNA isolation products and complete kits include Qiagen (Valencia, CA), Invitrogen (Carlsbad, CA), Ambion (Austin, TX) and Exiqon (Woburn, MA).

Generally, RNA isolation begins with tissue/cell destruction. It is desirable to minimize RNA degradation by RNase during tissue/cell destruction. One approach to limit RNase activity during the RNA isolation process is to ensure that a denaturing agent is kept in contact with cell contents as soon as the cells described above are destroyed. Another common practice is to include one or more proteases in the RNA isolation process. If necessary, fresh tissue samples are immersed in an RNA stabilizing solution at room temperature as soon as collected. The stabilizing solution rapidly permeates the cells and stabilizes the RNA for storage at 4° C. and subsequent isolation. One such stabilizing solution is commercially available as RNAlater® (Ambion, Austin, TX).

In some protocols, total RNA is isolated from the destroyed tumor material by cesium chloride density gradient centrifugation. Generally, mRNA constitutes about 1% to 5% of total cellular RNA. Immobilized oligo (dT) (e.g., oligo (dT) cellulose) is commonly used to separate mRNA from ribosomal RNA and transfer RNA. When stored after isolation, RNA must be stored under RNase-free conditions. Methods for stable storage of isolated RNA are known in the art. A variety of commercial products for stable storage of RNA are available.

Microarray

The expression level of mRNA can be determined (e.g., measured) using conventional DNA microarray expression profiling techniques. A DNA microarray is a collection of specific DNA segments or probes immobilized on a solid surface or support layer (e.g., glass, plastic or silicon), wherein each specific DNA segment occupies a known position in the array. Typically, hybridization with a sample of labeled RNA under stringent conditions allows detection and quantification of RNA molecules corresponding to each probe in the array described above. After stringent washing to remove non-specifically bound sample materials, the microarray is scanned by confocal laser microscopy or other suitable detection methods. Current commercially available DNA microarrays (often known as DNA chips) typically contain tens of thousands of probes and thus can simultaneously measure expression of tens of thousands of genes. Such microarrays can be used in the practice of the present invention. Alternatively, a bespoke chip including a number of probes required to measure expression of a specific gene and a control or standard as required (e.g., for data normalization) can be used in the practice of the methods of the present application.

A two-color microarray reader may be used to promote data normalization. In a two-color (two-channel) system, the sample is labeled with a first fluorophore that emits light at a first wavelength, while an RNA or cDNA standard is labeled with a second fluorophore that emits light at a different wavelength. For example, Cy3 (570 nm) and Cy5 (670 nm) are often used together in a two-color microarray system.

DNA microarray techniques are well developed, commercially available, and widely used. Thus, in practicing the methods of the present application, one skilled in the art can use microarray techniques to measure the expression level of a gene encoding a biomarker protein without undue experimentation. DNA microarray chips, reagents (e.g., necessary for RNA or cDNA preparation, RNA or cDNA labeling, hybridization solutions and cleaning solutions), equipment (e.g., microarray readers) and protocols are well known in the art and commercially available from various commercial sources. Examples of commercial vendors of microarray systems include Agilent Technologies, Inc. (Santa Clara, CA) and Affymetrix (Santa Clara, CA), but array systems from others can also be used.

Quantitative PCR

The level of mRNA can be measured using conventional quantitative reverse transcriptase polymerase chain reaction (qRT-PCR) techniques. Advantages of qRT-PCR include sensitivity, flexibility, quantitative accuracy, and the ability to distinguish between mRNAs with high sequence identity. Guidance on processing tissue samples for quantitative PCR is available from various sources (for example, manufacturers and vendors of apparatus and reagents for qRT-PCR, such as Qiagen (Valencia, CA) and Ambion (Austin, TX)). Equipment and systems for automatic operation of qRT-PCRs are commercially available, and are commonly used in many laboratories. Examples of well-known commercial systems include Applied Biosystems 7900HT Fast Real-Time PCR Systems (Applied Biosystems, Foster City, CA).

Once isolated mRNA is obtained, the first step of gene expression measurement by RT-PCR is to reverse transcribe the mRNA template to cDNA. The cDNA is then exponentially amplified in the PCR reaction. Two commonly used reverse transcriptases are avian myeloblastosis virus reverse transcriptase (AMV-RT) and moloney murine leukemia virus reverse transcriptase (MMLV-RT). The reverse transcription reaction is typically primed with a specific primer, a random hexamer, or an oligo(dT) primer. Suitable primers are commercially available (e.g., GeneAmp® RNA PCR kits (PerkinElmer Inc., Waltham, MA)). The obtained cDNA product can be used as a template in subsequent polymerase chain reactions.

The above PCR step is performed using a thermostable DNA-dependent DNA polymerase. The most commonly used polymerase in PCR systems is Thermus aquaticus (Taq) polymerase. The selectivity of the PCR results from the use of a primer that is complementary to the DNA region targeted for amplification (i.e., the region of cDNA reverse transcribed from the gene encoding the desired protein). Thus, when qRT-PCR is used in the present invention, the primer specific for each marker gene is based on the cDNA sequence of the gene described above. Commercial techniques (e.g., SYBR® Green or TaqMan® (Applied Biosystems, Foster City, CA)) may be used according to the vendor's instructions. The mRNA level may be normalized for differences in loading between samples by comparing the level to the level of a housekeeping gene (e.g., β-actin or GAPDH). The level of mRNA expression may be expressed relative to any single control sample (e.g., mRNA derived from a normal non-tumor tissue or cell). Alternatively, it may be expressed relative to mRNA derived from a pool of tumor samples, a tumor cell line, or a commercially available set of control mRNAs.

A suitable primer set for PCR analysis of the expression level of a gene can be designed and synthesized by one skilled in the art without undue experimentation.

Alternatively, a PCR primer set for carrying out the present invention can be purchased from commercial sources (e.g., Applied Biosystems). The PCR primer is preferably a primer of about 17 to 25 nucleotides in length. The primer can be designed to have a specific Tm using a conventional algorithm for melting temperature (Tm) estimation. Software for primer design and Tm estimation is commercially available (e.g., Primer Express™ (Applied Biosystems)) and is also available on the Internet (e.g., Primer 3 (Massachusetts Institute of Technology)). By applying established principles of PCR primer design, many different primers can be used to measure the expression level of any given gene.

qNPA

In some embodiments, RNA analysis is performed using techniques that do not include RNA extraction or isolation. One such technique is a quantitative nuclease protection assay commercially available under the name qNPA® (High Throughput Genomics, Inc., Tucson, AZ). This technique may be advantageous when the tissue sample to be analyzed is in the form of a FFPE material. See, e.g., Roberts et al, 2007, Laboratory Investigation 87:979-997.

nCounter Analysis System

The nCounter® is a system that directly counts molecules based on digital molecular barcoding technology, developed by NanoString Technologies, Inc., and enables up to 800 types of RNA and DNA to be analyzed quickly and accurately in a single tube. In the analysis of nCounter, a probe having a barcode specific for the sequence of the target molecule (reporter probe) and a probe for immobilization in the analysis cartridge (capture probe) are hybridized with the nucleic acid of the target, and the arrangement of colored barcodes for each target sequence immobilized on the surface of the cartridge is counted with a fluorescence scanner. See, e.g., Geiss G, et al., 26: 317-25 (2008), Nature Biotechnology.

HTG EdgeSeq Assays

EdgeSeq is an application for sample profiling including tumor profiling, molecular diagnostic testing, and development of biomarkers, consisting of measuring instruments, consumables and software analysis, developed by HTG Molecular Diagnostics, Inc. The molecular profiling of genes and genetic activity is automated by applying nuclease-protection chemistry to biological samples. See, e.g., Martel R., et al. Assay Drug Dev Technol. 2002 November; 1(1): 61-71. The amount of expression of individual genes is obtained by the above as a count value. The count values are used for analysis after normalization methods have been performed that correct variations in distribution between samples. Examples of specific normalization methods include the Median normalization method. In the Median normalization method, a scaling factor is determined for each sample by the method shown below, and a correction is made by dividing the amount of expression of a gene by the scaling factor. Scaling factor ($S_{ig}$) for $Gene_g$ of $Sample_i$ is the number obtained for the g-th gene ($Gene_g$) of the i-th sample ($Sample_i$) by determining a geometric mean of the amount of expression (count value) of all samples, and dividing the amount of expression of $Gene_g$ by the geometric mean. After the scaling factor is determined for all genes, the median $S_{ig}$ in $Sample_i$ is taken as the Scaling factor ($S_i$) of $Sample_i$. Finally, expression amounts of all genes of $Sample_i$ are divided by $S_i$ to obtain a value as a Median Normalized Count (MNC). For details of this technique, see, e.g., Andres, S. and Huber W Genome Biol. 2010; 11(10):R106.

Next-Generation RNA Sequencing

Unlike the conventional Sanger method, next-generation RNA sequencing is an RNA sequencing analysis employing next-generation sequencing techniques capable of obtaining an immense amount of sequence information in a short time and at a low cost by performing advanced parallelization processing. Next-generation RNA sequencing can analyze expression of the entire transcriptome with higher sensitivity and accuracy. Examples of typical next-generation sequencing techniques currently used include Sequencing by synthesis by Illumina Inc. and Ion Torrent technology by Thermo Fisher Scientific Inc. For details of each technique, see, e.g., Buermans H P., et al. Biochim Biophys Acta. 2014 October; 1842(10): 1932-1941. Individual sequence information (reads) obtained using the next-generation sequencing technique described above are also used for analysis after mapping work that identifies from which gene transcript each read is derived, and normalization procedures that correct the number of reads mapped to each transcript with the length of the transcript, the total number of reads obtained in the analysis, or the like. Specific examples of normalization procedures include a reads per kilobase of exon per million mapped sequence reads (RPKM) value, which is the number of reads corrected by the gene length of each gene when the length of transcript is set to 1 kb and the total number of reads is set to 1 million. Other examples which are generally used include a fragments per kilobase of exon per million mapped sequence reads (FPKM) value, which is the number of fragments corrected by the gene length of each gene when the total number of reads is set to 1 million, and a transcripts per million (TPM) value, which is the number of transcripts when the number of reads of each transcript is corrected by the gene length and the total number of reads is set to 1 million. RPKM is obtained by calculating the amount of expression per gene by counting reads mapped to exons using a known genetic model, while FPKM is obtained by calculating the amount of expression at isoform level by counting fragments per estimated isoform. For details of the techniques for each normalization, see, e.g., Conesa A., et al. Genome Biol. 2016 Jan. 26; 17:13.

Evaluation of hTROP2 Gene Expression hTROP2 gene expression can be evaluated in biological samples from human patients. Such embodiments include requesting evaluation of hTROP2 gene expression at mRNA level and receiving a result of the evaluation. Some embodiments include determining a numerical value of hTROP2 gene expression at mRNA level and recording the determined numerical value by any method.

The expression level of the hTROP2 gene can be interpreted in relation to a predetermined numerical value. When the expression level of the hTROP2 gene is equal to, greater than or equal to, or exceeds a predetermined numerical value, the expression level of the hTROP2 gene is interpreted as being capable of predicting that the subject is sensitive (responsive) to a treatment with a medicament containing an anti-hTROP2 antibody. In some embodiments, when the expression level of the hTROP2 gene is equal to, less than or equal to, or below a predetermined numerical value, the expression level of the hTROP2 gene is interpreted as being capable of predicting that the tumor is resistant (non-responsive) to a treatment with a medicament containing an anti-hTROP2 antibody.

In some embodiments, the hTROP2 gene expression may be evaluated to be high or low, based on numerical values representing the expression level of the hTROP2 gene in the biological sample. A subject can be evaluated as having high or low expression based on, for example, the hTROP2 expression at mRNA level.

The expression level can be evaluated by any known method as described above. For example, the amount of expression of the hTROP2 gene can be evaluated based on a reads per kilobase of exon per million mapped sequence reads (RPKM) value calculated by next-generation RNA sequencing. The RPKM value is a value obtained by normalizing the number of reads obtained with the next-generation sequencer using the exon length of each gene and the total number of sequences read with the sequencer. The amount of expression of the hTROP2 gene can be analyzed by using a $\log_2[\text{RPKM}+1]$ value that is a value obtained by adding 1 to the RPKM value, and transforming the sum to a logarithmic ($\log_2$).

The RPKM value is correlated with hTROP2 gene expression. Thus, the higher the RPKM value, the higher the hTROP2 gene expression. In some embodiments, when the $\log_2[\text{RPKM}+1]$ value is greater than or equal to, or exceeds a predetermined numerical value, the hTROP2 gene expression is evaluated to be high. The predetermined numerical value may be statistically specified to minimize the undesirable effects of false positives and false negatives. The specified numerical value can be selected from the range of 6.0 to 9.0. For example, the specified numerical value can be selected from the group consisting of 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, and 9.0. The specified numerical value can also be selected from the range of 6.0 to 8.0. For example, the specified numerical value can be selected from the group consisting of 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0. The specified numerical value can further be selected from the range of 6.5 to 8.0. For example, the specified numerical value can be selected from the group consisting of 6.5, 6.6, 6.7, 6.8, 6.9, 7.0, 7.1, 7.2, 7.3, 7.4, 7.5, 7.6, 7.7, 7.8, 7.9, and 8.0. The specified numerical value can still further be selected from the range of 7.0 to 8.0. For example, the specified numerical value can be selected from the group consisting of 7.0, 7.1, 7.2, 7.3, 7.4, 7.5, 7.6, 7.7, 7.8, 7.9, and 8.0. The specified numerical value can still further be selected from the range of 7.5 to 8.0. For example, the specified numerical value can be selected from the group consisting of 7.5, 7.6, 7.7, 7.8, 7.9, and 8.0. The specified numerical value can also be selected from the group consisting of 6.5, 7.0, 7.5, and 8.0.

The amount of expression of the hTROP2 gene can be evaluated based on a fragments per kilobase of exon per million mapped sequence reads (FPKM) value calculated by next-generation RNA sequencing. The FPKM value is a value obtained by normalizing the number of reads obtained with the next generation sequencer using the gene length of each gene and the total number of sequences read with the sequencer. The amount of expression of the hTROP2 gene can be analyzed by using a $\log_2[\text{FPKM}+1]$ value that is a value obtained by adding 1 to the FPKM value, and transforming the sum to a logarithmic ($\log_2$).

The FPKM value is correlated with hTROP2 gene expression. Thus, the higher the FPKM value, the higher the hTROP2 gene expression. In some embodiments, when the $\log_2[\text{FPKM}+1]$ value is greater than or equal to, or exceeds a predetermined numerical value, the hTROP2 gene expression is evaluated to be high. The predetermined numerical value may be statistically specified to minimize the undesirable effects of false positives and false negatives. The specified numerical value can be selected from the range of 6.0 to 8.0. For example, the specified numerical value can be selected from the group consisting of 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0. The specified numerical value can also be selected from the range of 6.0 to 7.0. For example, the specified numerical value can be selected from the group consisting of 6.0, 6.1, 6.2, 6.3, 6.4, 6.5, 6.6, 6.7, 6.8, 6.9, and 7.0. The specified numerical value can also be selected as 6.0 or 7.0.

The amount of expression of the hTROP2 gene can be evaluated based on a Median Normalized Count (MNC) value calculated by an EdgeSeq Assay. The MNC value is a value obtained by the Median normalization method in the EdgeSeq Assay. The amount of expression of the hTROP2 gene can be analyzed by using a $\log_2[\text{MNC}+1]$ value that is a value obtained by adding 1 to the MNC value, and transforming the sum to a logarithmic ($\log_2$).

The MNC value is correlated with hTROP2 gene expression. Thus, the higher the MNC value, the higher the hTROP2 gene expression. In some embodiments, when the $\log_2[\text{MNC}+1]$ value is greater than or equal to, or exceeds a predetermined numerical value, the hTROP2 gene expression is evaluated to be high. The predetermined numerical value may be statistically specified to minimize the undesirable effects of false positives and false negatives. The specified numerical value can be selected from the range of 12.0 to 15.0. For example, the specified numerical value can be selected from the group consisting of 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, and 15.0. The specified numerical value can also be selected from the range of 12.0 to 14.0.

For example, the specified numerical value can be selected from the group consisting of 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, and 14.0. The specified numerical value can also be selected as 12.0, 13.0, or 14.0.

In some embodiments, hTROP2 gene expression at mRNA level is evaluated using a testing method approved by a regulatory authority. In some embodiments, the testing method approved by a regulatory authority is a testing method approved by FDA, EMA, or PMDA.

Evaluation of SLFN11 Gene Expression

SLFN11 gene expression can be evaluated in biological samples from human patients. Such embodiments include requesting evaluation of SLFN11 gene expression at mRNA level and receiving a result of the evaluation. Some embodiments include determining a numerical value of SLFN11 gene expression at mRNA level and recording the determined numerical value by any method.

The expression level of the SLFN11 gene can be interpreted in relation to a predetermined numerical value. When the expression level of the SLFN11 gene is equal to, greater than or equal to, or exceeds a predetermined numerical value, the expression level of the SLFN11 gene is interpreted as being capable of predicting that the subject is sensitive (responsive) to a treatment with a medicament containing an anti-hTROP2 antibody. In some embodiments, when the expression level of the SLFN11 gene is equal to, less than or equal to, or below a predetermined numerical value, the expression level of the SLFN11 gene is interpreted as being capable of predicting that the tumor is resistant (non-responsive) to a treatment with a medicament containing an anti-hTROP2 antibody.

In some embodiments, the SLFN11 gene expression may be evaluated to be high or low, based on numerical values representing the expression level of the SLFN11 gene in the biological sample. A subject can be evaluated as having high or low expression based on, for example, the SLFN11 expression at mRNA level.

The expression level can be evaluated by any known method as described above. For example, the amount of expression of the SLFN11 gene can be evaluated based on a RPKM value in the same manner as that of the hTROP2 gene.

The amount of expression of the SLFN11 gene can be analyzed by using a $\log_2[\text{RPKM}+1]$ value that is a value obtained by adding 1 to the RPKM value, and transforming the sum to a logarithmic ($\log_2$).

The RPKM value is correlated with SLFN11 gene expression. Thus, the higher the RPKM value, the higher the SLFN11 gene expression. In some embodiments, when the $\log_2[\text{RPKM}+1]$ value exceeds a predetermined numerical value, the SLFN11 gene expression is evaluated to be high. The predetermined numerical value may be statistically specified to minimize the undesirable effects of false positives and false negatives. The specified numerical value can be selected from the range of 1.0 to 4.0. For example, the specified numerical value can be selected from the group consisting of 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0. The specified numerical value can also be selected from the range of 1.0 to 3.0. For example, the specified numerical value can be selected from the group consisting of 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0. The specified numerical value can further be selected from the range of 2.0 to 3.0. For example, the specified numerical value can be selected from the group consisting of 2.0, 2.1, 2.2, 2.3, 2.4, 2.5, 2.6, 2.7, 2.8, 2.9, and 3.0. The specified numerical value can be selected from the group consisting of 1.0, 2.0, and 3.0, and can also be specified as 3.0.

The amount of expression of the SLFN11 gene can be evaluated based on a FPKM value in the same manner as that of the hTROP2 gene. The amount of expression of the SLFN11 gene can be analyzed by using a $\log_2[\text{FPKM}+1]$ value that is a value obtained by adding 1 to the FPKM value, and transforming the sum to a logarithmic ($\log_2$).

The FPKM value is correlated with SLFN11 gene expression. Thus, the higher the FPKM value, the higher the SLFN11 gene expression. In some embodiments, when the $\log_2[\text{FPKM}]$ value exceeds a predetermined numerical value, the SLFN11 gene expression is evaluated to be high. The predetermined numerical value may be statistically specified to minimize the undesirable effects of false positives and false negatives. The specified numerical value can be selected from the range of 2.0 to 4.0. For example, the specified numerical value can be selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0. The specified numerical value can also be selected from the range of 2.0 to 3.0. For example, the specified numerical value can be selected from the group consisting of 2.0, 2.1, 2.2, 2.3, 2.4, 2.5, 2.6, 2.7, 2.8, 2.9, and 3.0. The specified numerical value can be selected as 2.0 or 3.0.

The amount of expression of the SLFN11 gene can be evaluated based on an MNC value in the same manner as that of the hTROP2 gene. The amount of expression of the SLFN11 gene can be analyzed by using a $\log_2[\text{MNC}+1]$ value that is a value obtained by adding 1 to the MNC value, and transforming the sum to a logarithmic ($\log_2$).

The MNC value is correlated with SLFN11 gene expression. Thus, the higher the MNC value, the higher the SLFN11 gene expression. In some embodiments, when the $\log_2[\text{MNC}]$ value exceeds a predetermined numerical value, the SLFN11 gene expression is evaluated to be high. The predetermined numerical value may be statistically specified to minimize the undesirable effects of false positives and false negatives. The specified numerical value can be selected from the range of 11.5 to 13.5. For example, the specified numerical value can be selected from the group consisting of 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, and 13.5. The specified numerical value can also be selected from the range of 11.5 to 12.5. For example, the specified numerical value can be selected from the group consisting of 11.5, 11.6, 11.7, 11.8, 11.9, 12.0, 12.1, 12.2, 12.3, 12.4, and 12.5. The specified numerical value can be selected as 11.5, 12.0, or 12.5.

In some embodiments, SLFN11 gene expression at mRNA level is evaluated using a testing method approved by a regulatory authority. In some embodiments, the testing method approved by a regulatory authority is a testing method approved by FDA, EMA, or PMDA.

Administration and Treatment

In some embodiments, evaluation of hTROP2 gene expression can be evaluated in combination with SLFN11 gene expression. The combination of the two sensitivity markers enables a more accurate evaluation. In some embodiments, a human patient suffering from a cancer may be given and treated with a medicament containing an anti-hTROP2 antibody when the expression of the hTROP2 gene and/or the SLFN11 gene has been evaluated to be high. In some embodiments, administration of a medicament containing an anti-hTROP2 antibody to a human patient suffering from a cancer may be avoided when the expression of the hTROP2 gene and/or the SLFN11 gene has been evaluated to be low.

Examples of preferred dosages of a medicament containing an anti-hTROP2 antibody include, but are not limited to, 2.0 mg/kg, 4.0 mg/kg, 6.0 mg/kg, 8.0 mg/kg, or 10.0 mg/kg. Also, examples of preferred dosing intervals of a medicament containing an anti-hTROP2 antibody include, but are not limited to, 3-week intervals.

The amount of expression of the hTROP2 and SLFN11 genes can be evaluated based on RPKM values. The amount of expression of each gene can be analyzed by using a $\log_2[\text{RPKM}+1]$ value that is a value obtained by adding 1 to the RPKM value, and transforming the sum to a logarithmic ($\log_2$). The predetermined numerical value may be statistically specified to minimize the undesirable effects of false positives and false negatives.

As described above, the $\log_2[\text{RPKM}+1]$ value of the hTROP2 gene can be specified in the range of 6.0 to 9.0. The $\log_2[\text{RPKM}+1]$ value of the SLFN11 gene can also be specified in the range of 1.0 to 4.0. When the combination of the specified numerical values is used, a human patient suffering from a cancer may be given and treated with a medicament containing an anti-hTROP2 antibody when both of the hTROP2 and SLFN11 genes meet the specified values. In some embodiments, a human patient suffering from a cancer may be given and treated with a medicament containing an anti-hTROP2 antibody when either one of the hTROP2 and SLFN11 genes meets the specified value.

Examples of preferred combinations of the specified $\log_2[\text{RPKM}+1]$ values of the hTROP2 and SLFN11 genes include: a combination of one value selected from the group consisting of 7.5, 7.6, 7.7, 7.8, 7.9, and 8.0 of the hTROP2 gene and one value selected from the group consisting of 1.0, 1.1, 1.2, 1.3, 1.4, 1.5, 1.6, 1.7, 1.8, 1.9, and 2.0 of the SLFN11 gene; a combination of one value selected from the group consisting of 6.5, 6.6, 6.7, 6.8, 6.9, and 7.0 of the hTROP2 gene and one value selected from the group consisting of 2.0, 2.1, 2.2, 2.3, 2.4, 2.5, 2.6, 2.7, 2.8, 2.9, and 3.0 of the SLFN11 gene; and a combination of one value selected from the group consisting of 7.0, 7.1, 7.2, 7.3, 7.4, and 7.5 of the hTROP2 gene and one value selected from the group consisting of 2.0, 2.1, 2.2, 2.3, 2.4, 2.5, 2.6, 2.7, 2.8, 2.9, and 3.0 of the SLFN11 gene.

Other examples of preferred combinations of the specified $\log_2[\text{RPKM}+1]$ values of the hTROP2 gene and the SLFN11 gene include: a combination of one value selected from the group consisting of 7.5, 7.6, 7.7, 7.8, 7.9, and 8.0 of the hTROP2 gene and one value selected from the group consisting of 2.0, 2.1, 2.2, 2.3, 2.4, 2.5, 2.6, 2.7, 2.8, 2.9, and 3.0 of the SLFN11 gene; a combination of one value selected from the group consisting of 6.5, 6.6, 6.7, 6.8, 6.9, and 7.0 of the hTROP2 gene and one value selected from the group consisting of 3.0, 3.1, 3.2, 3.3, 3.4, 3.5, 3.6, 3.7, 3.8, 3.9, and 4.0 of the SLFN11 gene; a combination of one value selected from the group consisting of 7.5, 7.6, 7.7, 7.8, 7.9, and 8.0 of the hTROP2 gene and one value selected from the group consisting of 3.0, 3.1, 3.2, 3.3, 3.4, 3.5, 3.6, 3.7, 3.8, 3.9, and 4.0 of the SLFN11 gene.

Examples of further preferred combinations of the specified $\log_2[\text{RPKM}+1]$ values of the hTROP2 gene and the SLFN11 gene include a case in which either one of a combination of 7.5 of the hTROP2 gene and 1.0 of the SLFN11 gene or a combination of 6.5 of the hTROP2 gene and 2.0 of the SLFN11 gene is met.

Other examples of further preferred combinations of the specified $\log_2[\text{RPKM}+1]$ values of the hTROP2 gene and the SLFN11 gene include a case in which either one of a combination of 7.5 of the hTROP2 gene and 2.0 of the SLFN11 gene or a combination of 6.5 of the hTROP2 gene and 3.0 of the SLFN11 gene is met.

Other examples of further preferred combinations of the specified $\log_2[\text{RPKM}+1]$ values of the hTROP2 gene and the SLFN11 gene include any one combination selected from the group consisting of a combination of 7.5 of the hTROP2 gene and 1.0 of the SLFN11 gene, a combination of 6.5 of the hTROP2 gene and 2.0 of the SLFN11 gene, a combination of 7.5 of the hTROP2 gene and 2.0 of the SLFN11 gene, and a combination of 6.5 of the hTROP2 gene and 3.0 of the SLFN11 gene.

The amount of expression of the hTROP2 and SLFN11 genes can also be evaluated based on FPKM values. The amount of expression of each gene can be analyzed by using a $\log_2[\text{FPKM}+1]$ value that is a value obtained by adding 1 to the FPKM value, and transforming the sum to a logarithmic ($\log_2$). The predetermined numerical value may be statistically specified to minimize the undesirable effects of false positives and false negatives.

As described above, the $\log_2[\text{FPKM}+1]$ value of the hTROP2 gene can be specified in the range of 6.0 to 8.0. The $\log_2[\text{FPKM}+1]$ value of the SLFN11 gene can also be specified in the range of 2.0 to 4.0. When the combination of the specified numerical values is used, a human patient suffering from a cancer may be given and treated with a medicament containing an anti-hTROP2 antibody when both of the hTROP2 and SLFN11 genes meet the specified values. In some embodiments, a human patient suffering from a cancer may be given and treated with a medicament containing an anti-hTROP2 antibody when either one of the hTROP2 and SLFN11 genes meets the specified value.

Examples of preferred combinations of the specified $\log_2[\text{FPKM}+1]$ values of the hTROP2 and SLFN11 genes include a combination of one value selected from the group consisting of 7.0, 7.1, 7.2, 7.3, 7.4, 7.5, 7.6, 7.7, 7.8, 7.9, and 8.0 of the hTROP2 gene and one value selected from the group consisting of 2.0, 2.1, 2.2, 2.3, 2.4, 2.5, 2.6, 2.7, 2.8, 2.9, and 3.0 of the SLFN11 gene.

Other examples of preferred combinations include a combination of one value selected from the group consisting of 6.0, 6.1, 6.2, 6.3, 6.4, 6.5, 6.6, 6.7, 6.8, 6.9, and 7.0 of the hTROP2 gene and one value selected from the group consisting of 3.0, 3.1, 3.2, 3.3, 3.4, 3.5, 3.6, 3.7, 3.8, 3.9, and 4.0 of the SLFN11 gene.

Still other examples of preferred combinations include a combination of one value selected from the group consisting of 7.0, 7.1, 7.2, 7,3, 7.4, 7.5, 7.6, 7.7, 7.8, 7.9, and 8.0 of the hTROP2 gene and one value selected from the group consisting of 3.0, 3.1, 3.2, 3.3, 3.4, 3.5, 3.6, 3.7, 3.8, 3.9, and 4.0 of the SLFN11 gene.

Other examples of further preferred combinations of the specified $\log_2$[FPKM+1] values of the hTROP2 gene and the SLFN11 gene include any one combination selected from the group consisting of a combination of 7.0 of the hTROP2 gene and 2.0 of the SLFN11 gene, a combination of 6.0 of the hTROP2 gene and 3.0 of the SLFN11 gene, and a combination of 7.0 of the hTROP2 gene and 3.0 of the SLFN11 gene.

The amount of expression of the hTROP2 and SLFN11 genes can be further evaluated based on MNC values. The amount of expression of each gene can be analyzed by using a $\log_2$[MNC+1] value that is a value obtained by adding 1 to the MNC value, and transforming the sum to a logarithmic ($\log_2$). The predetermined numerical value may be statistically specified to minimize the undesirable effects of false positives and false negatives.

As described above, the $\log_2$[MNC+1] value of the hTROP2 gene can be specified in the range of 12.0 to 15.0. The $\log_2$[MNC+1] value of the SLFN11 gene can also be specified in the range of 11.5 to 13.5. When the combination of the specified numerical values is used, a human patient suffering from a cancer may be given and treated with a medicament containing an anti-hTROP2 antibody when both of the hTROP2 and SLFN11 genes meet the specified values. In some embodiments, a human patient suffering from a cancer may be given and treated with a medicament containing an anti-hTROP2 antibody when either one of the hTROP2 and SLFN11 genes meets the specified value.

Examples of preferred combinations of the specified $\log_2$[MNC+1] values of the hTROP2 and SLFN11 genes include a combination of one value selected from the group consisting of 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, and 15.0 of the hTROP2 gene and one value selected from the group consisting of 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, and 13.5 of the SLFN11 gene.

Other examples of preferred combinations include a combination of one value selected from the group consisting of 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, and 14.0 of the hTROP2 gene and one value selected from the group consisting of 11.5, 11.6, 11.7, 11.8, 11.9, 12.0, 12.1, 12.2, 12.3, 12.4, and 12.5 of the SLFN11 gene.

Still other examples of the combinations include a combination of one value selected from 12.0, 13.0, or 14.0 of the hTROP2 gene and one value selected from 11.5, 12.0, or 12.5 of the SLFN11 gene.

Other examples of further preferred combinations of the specified $\log_2$[MNC+1] values of the hTROP2 gene and the SLFN11 gene include any one combination selected from the group consisting of a combination of 12.0 of the hTROP2 gene and 11.5 of the SLFN11 gene, a combination of 14.0 of the hTROP2 gene and 11.5 of the SLFN11 gene, a combination of 12.0 of the hTROP2 gene and 12.5 of the SLFN11 gene, and a combination of 14.0 of the hTROP2 gene and 12.5 of the SLFN11 gene.

The measurement and evaluation of gene expression can be performed simultaneously for the hTROP2 gene and the SLFN11 gene.

Alternatively, the measurement and evaluation of the amount of expression of the hTROP2 gene may be firstly performed, and then, for a human patient in whom the amount of expression of the hTROP2 gene has been evaluated to be high, the measurement and evaluation of the amount of expression of the SLFN11 gene may be performed.

Alternatively, the measurement and evaluation of the amount of expression of the SLFN11 gene may be firstly performed, and then, for a human patient in whom the amount of expression of the SLFN11 gene has been evaluated to be high, the measurement and evaluation of the amount of expression of the hTROP2 gene may be performed.

In some embodiments, hTROP2 and SLFN11 gene expression at mRNA level are evaluated using a testing method approved by a regulatory authority. In some embodiments, the testing method approved by a regulatory authority is a testing method approved by FDA, EMA, or PMDA.

Test Kit

The present invention also relates to a diagnostic test kit comprising several configurations for carrying out the methods of the present invention. The diagnostic test kit improves the convenience, rapidity, and reproducibility when performing diagnostic assays. For example, in embodiments based on qRT-PCR, a basic diagnostic test kit includes a PCR primer that analyzes expression of a gene. In other embodiments, a more specific test kit includes, in addition to a PCR primer, a buffering agent, a reagent, and detailed instructions for measuring gene expression levels using PCR techniques. In some embodiments, the kit includes a test protocol and all consumables other than the RNA sample which are necessary for the testing.

EXAMPLES

The present invention is described in detail by the following Examples, but the present invention is not limited by these Examples.

Example 1. Production of Antibody-Drug Conjugate

An antibody-drug conjugate in which a drug-linker represented by the formula:

[Formula 7]

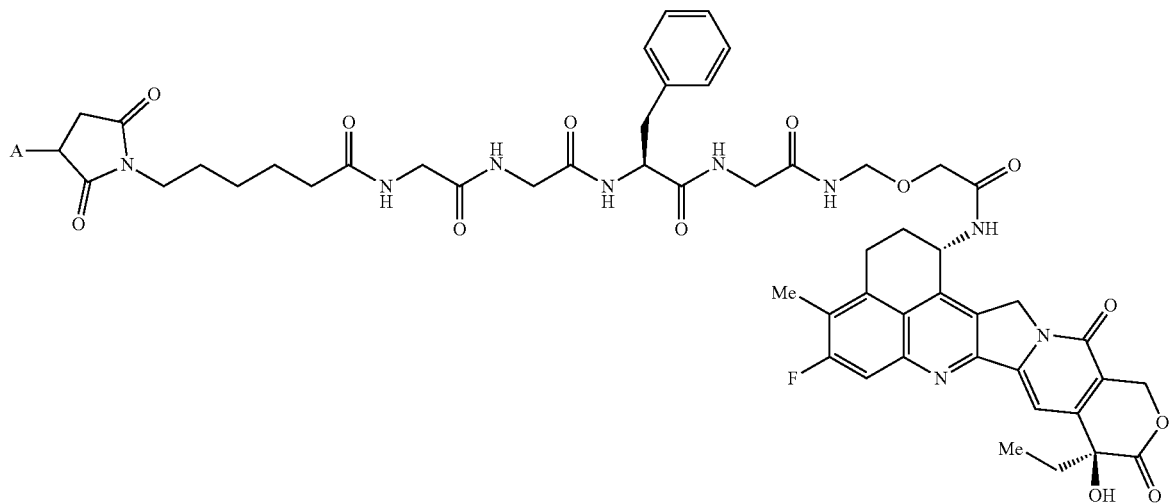

wherein A represents a connecting position to an anti-hTROP2 antibody, and an anti-hTROP2 antibody are conjugated to each other via a thioether bond was produced using a humanized anti-hTROP2 antibody (antibody comprising a heavy chain consisting of an amino acid sequence consisting of amino acid residues 20 to 470 of SEQ ID NO: 1 and a light chain consisting of an amino acid sequence consisting of amino acid residues 21 to 234 of SEQ ID NO: 2), according to the production methods described in WO 2015/098099 and WO 2017/002776 (hereinafter, the antibody-drug conjugate is referred to as antibody-drug conjugate (1)). Although the average number of conjugated drugs per antibody molecule could be adjusted in the range of 0 to 8, an antibody-drug conjugate with an average number of drug conjugates of 3.5 to 4.5 was produced this time and used in the following Examples.

Example 2. Evaluation of Anti-Tumor Effects of Antibody-Drug Conjugate (1)

Mice: Female nu/nu mice (Envigo) aged 5-8 weeks were acclimatized under SPF conditions for 3 days or more prior to experimental use. Mice were fed with sterile solid feed (Teklad2919, Envigo) and given reverse osmosis membrane-treated water (containing 2 ppm chlorine).

Measurements and Calculation formula: long and short diameters of tumors were measured twice a week with an electronic digital caliper (CD-6PMX, Mitutoyo Corp.) and tumor volume ($mm^3$) was calculated using the following calculation formula:

Tumor volume ($mm^3$)=0.52×Long diameter (mm)× [Short diameter (mm)]$^2$

Tumor fragments from each cancer patient were subcutaneously implanted into mice and passaged. The obtained tumors were used to subcutaneously implant tumor fragments, which were cut to approximately 5×5×5 $mm^3$, into the left abdomen of the female nu/nu mice, thereby each patient-derived xenograft (PDX) model was created. Mice were randomly grouped when the mean transplanted tumor volume reached 150 to 300 $mm^3$ (Day 0). On the same day as grouping, the antibody-drug conjugate (1) was administered into the tail vein at a dose of 10 mg/kg. A formulation buffer was similarly administered at a volume of 10 mL/kg as a negative control. Tumor growth inhibition rates (TGI (%)) were calculated according to the following calculation formula using each tumor volume 21 days after administration (Table 1).

Tumor growth inhibition rate (%)=100×(1−$Tf$/mean $Cf$)

Tf: tumor volume 21 days after administration of antibody-drug conjugate (1)

mean Cf: arithmetic mean tumor volume 21 days after administration in negative control group mice All the above tests were performed at Champions Oncology, Inc.

TABLE 1

Anti-tumor activity (TGI %) of antibody-drug conjugate (1) in each PDX model

| Model ID | Carcinoma | TGI (%) |
|---|---|---|
| #1 | Breast | 98.1 |
| #2 | Lung | 77.3 |
| #3 | Cholangiocarcinoma | 48.0 |
| #4 | Pancreatic | 48.5 |
| #5 | Colorectal | 65.0 |
| #6 | Breast | 95.5 |
| #7 | Breast | 94.7 |
| #8 | Head and neck | 55.6 |
| #9 | Head and neck | 99.1 |
| #10 | Lung | 97.7 |
| #11 | Lung | 95.4 |
| #12 | Breast | 95.8 |
| #13 | Lung | 70.0 |
| #14 | Breast | 90.1 |
| #15 | Cholangiocarcinoma | 61.2 |
| #16 | Colorectal | 52.7 |
| #17 | Breast | 62.6 |
| #18 | Lung | 18.4 |
| #19 | Lung | 50.3 |

Example 3. hTROP2 and SLFN11 Gene Expression (RPKM Values) in Tumors Derived from Each PDX Mouse Model, and the Relationship Thereof with the Anti-Tumor Activity of Antibody-Drug Conjugate (1)

Data on the amount of gene expression in each PDX model used in Example 2 were obtained and normalized at Champions Oncology, Inc., thereby a RPKM value was obtained. To the RPKM value, 1 was added, and the sum was transformed to a logarithmic ($\log_2$) to obtain a $\log_2$[RPKM+1] value (Table 2). The $\log_2$[RPKM+1] value was used to analyze the relationship between the anti-tumor activity of antibody-drug conjugate (1) in each PDX model (Table 1) and the amount of expression of the hTROP2 gene and the SLFN11 gene. When all of the evaluated models were grouped into groups having at least a certain amount of expression of the hTROP2 and SLFN11 genes (Table 3), it was shown that the proportion of animal models showing at least a certain drug efficacy (in this case, a criterion of TGI of 75% or more was employed as an example) is higher as the hTROP2 gene expression and the SLFN11 gene expression increases (Table 4). In the absence of grouping by SLFN11 gene expression, the proportion of animal models showing TGI of 75% or more was not more than 47 to 63%. Thus, it was revealed that a combination of the amount of hTROP2 gene expression and the amount of SLFN11 gene expression can be used as a sensitivity marker to predict the anti-tumor effect of antibody-drug conjugate (1). For example, when the $\log_2$[RPKM+1] value of the hTROP2 gene exceeds 7.5 and the $\log_2$[RPKM+1] value of the SLFN11 gene exceeds 1.0, or when the $\log_2$[RPKM+1] value of the hTROP2 gene exceeds 6.5 and the $\log_2$[RPKM+1] of the SLFN11 gene exceeds 2.0, the proportion of animal models showing TGI of 75% or more is about 80% to 100%. Furthermore, when the $\log_2$[RPKM+1] value of the hTROP2 gene exceeds 7.5 and the $\log_2$[RPKM+1] value of the SLFN11 gene exceeds 2.0, or when the $\log_2$[RPKM+1] value of the hTROP2 gene exceeds 6.5 and the $\log_2$[RPKM+1] of the SLFN11 gene exceeds 3.0, the proportion of animal models showing TGI of 75% or more is 100%. It should be noted that even when TGI was 60% or more or 70% or more, it was possible to predict anti-tumor effects at comparable prediction rates using each $\log_2$[RPKM+1] value which was specified when TGI was 75% or more. When TGI was 80% or more, the prediction rate decreased to an order of 60% only when the $\log_2$[RPKM+1] value of the hTROP2 gene exceeded 7.5 and the $\log_2$[RPKM+1] value of the SLFN11 gene exceeded 1.0 and was less than or equal to 2.

TABLE 2 hTROP2 gene and SLFN11 gene expression in each PDX model

| Model ID | hTROP2 gene expression amount ($\log_2$ [RPKM + 1]) | SLFN11 gene expression amount ($\log_2$ [RPKM + 1]) |
|---|---|---|
| #1 | 7.05 | 3.41 |
| #2 | 8.37 | 1.59 |
| #3 | 8.09 | 0.16 |
| #4 | 8.25 | 0.40 |
| #5 | 6.72 | 0.09 |
| #6 | 6.99 | 0.00 |
| #7 | 5.27 | 0.67 |
| #8 | 8.73 | 1.66 |
| #9 | 8.13 | 4.15 |
| #10 | 8.25 | 3.42 |
| #11 | 6.28 | 4.05 |
| #12 | 7.68 | 2.31 |
| #13 | 4.89 | 5.00 |
| #14 | 8.39 | 2.03 |
| #15 | 6.69 | 0.01 |
| #16 | 6.80 | 1.09 |
| #17 | 6.10 | 2.78 |
| #18 | 7.29 | 1.74 |
| #19 | 7.10 | 2.83 |

TABLE 3

Number of PDX models having at least a certain amount of expression of the hTROP2 gene and the SLFN11 gene

| hTROP2 gene expression amount ($\log_2$ [RPKM + 1]) | SLFN11 gene expression amount ($\log_2$ [RPKM + 1]) | | | |
|---|---|---|---|---|
| | All models | >1 | >2 | >3 |
| All models | 19 | 13 | 9 | 5 |
| >6.5 | 15 | 10 | 6 | 3 |
| >7.0 | 11 | 9 | 6 | 3 |
| >7.5 | 8 | 6 | 4 | 2 |
| >8.0 | 7 | 5 | 3 | 2 |

TABLE 4

Proportion of PDX models showing TGI of 75% or more by antibody-drug conjugate (1) in PDX models having at least a certain amount of expression of the hTROP2 gene and the SLFN11 gene

| hTROP2 gene expression amount ($\log_2$ [RPKM + 1]) | SLFN11 gene expression amount ($\log_2$ [RPKM + 1]) | | | |
|---|---|---|---|---|
| | All models | >1 | >2 | >3 |
| All models | 47% | 54% | 67% | 80% |
| >6.5 | 47% | 60% | 83% | 100% |
| >7.0 | 55% | 67% | 83% | 100% |
| >7.5 | 63% | 83% | 100% | 100% |
| >8.0 | 57% | 80% | 100% | 100% |

Example 4. Evaluation of Anti-Tumor Effects of Antibody-Drug Conjugate (2)

Mice: Female nu/nu mice (Envigo) aged 5-8 weeks were acclimatized under SPF conditions for 3 days or more prior to experimental use. Mice were fed with sterile solid feed (Teklad2919, Envigo) and given reverse osmosis membrane-treated water (containing 2 ppm chlorine).

Measurements and Calculation formula: long and short diameters of tumors were measured twice a week with an electronic digital caliper (CD-6PMX, Mitutoyo Corp.) and tumor volume (mm$^3$) was calculated using the following calculation formula:

$$\text{Tumor volume (mm}^3\text{)} = 0.52 \times \text{Long diameter (mm)} \times [\text{Short diameter (mm)}]^2$$

Tumor fragments from each cancer patient were subcutaneously implanted into mice and passaged. The obtained tumors were used to subcutaneously implant tumor fragments, which were cut to approximately 5×5×5 mm$^3$, into the left abdomen of female nu/nu mice, thereby each patient-derived xenograft (PDX) model was created. Mice were randomly grouped when the mean transplanted tumor volume reached 150 to 300 mm³ (Day 0). On the same day as grouping, the antibody-drug conjugate (1) was administered into the tail vein at a dose of 10 mg/kg. A formulation buffer was similarly administered at a volume of 10 mL/kg as a negative control.

For the PDX models evaluated in Example 2 and in this Example, tumor growth inhibition rates (TGI (%)) were calculated according to the following calculation formula using each tumor volume 10 to 15 days after administration (Table 5).

Tumor growth inhibition rate (%)=100×(1−$Tf$/mean $Cf$)

Tf: tumor volume 10 to 15 days after administration of antibody-drug conjugate (1)
mean Cf: arithmetic mean tumor volume 10 to 15 days after administration in negative control group mice

TABLE 5

Anti-tumor activity (TGI %) of antibody-drug conjugate (1) in each PDX model

| Model ID | Cancer species | TGI (%) | Evaluation time point |
|---|---|---|---|
| #1 | Breast | 95.2 | Day 14 |
| #2 | Lung | 68.3 | Day 14 |
| #3 | Cholangiocarcinoma | 22.2 | Day 14 |
| #4 | Pancreatic | 21.8 | Day 14 |
| #5 | Colorectal | 41.7 | Day 14 |
| #6 | Breast | 92.4 | Day 14 |
| #7 | Breast | 87.6 | Day 15 |
| #8 | Head & neck | 57.9 | Day 14 |
| #9 | Head & neck | 94.0 | Day 14 |
| #10 | Lung | 97.3 | Day 14 |
| #11 | Lung | 87.4 | Day 14 |
| #12 | Breast | 90.0 | Day 15 |
| #13 | Lung | 62.3 | Day 14 |
| #14 | Breast | 82.7 | Day 14 |
| #15 | Cholangiocarcinoma | 46.4 | Day 14 |
| #16 | Colorectal | 26.0 | Day 14 |
| #17 | Breast | 56.5 | Day 14 |
| #18 | Lung | 14.6 | Day 14 |
| #19 | Lung | 28.1 | Day 14 |
| #20 | Lung | 82.0 | Day 14 |
| #21 | Lung | 76.6 | Day 14 |
| #22 | Lung | 87.9 | Day 14 |
| #23 | Lung | 4.7 | Day 14 |
| #24 | Lung | 19.1 | Day 14 |
| #25 | Pancreatic | 37.9 | Day 14 |
| #26 | Pancreatic | 62.3 | Day 13 |
| #27 | Lung | 48.5 | Day 13 |
| #28 | Breast | 92.6 | Day 14 |
| #29 | Breast | 97.4 | Day 14 |
| #30 | Lung | 84.7 | Day 10 |
| #31 | Colorectal | 58.4 | Day 14 |
| #32 | Lung | 64.9 | Day 13 |
| #33 | Lung | 25.0 | Day 14 |
| #34 | Lung | 89.7 | Day 13 |
| #35 | Lung | −0.4 | Day 14 |

Example 5. hTROP2 and SLFN11 Gene Expression (FPKM Values) in Tumors Derived from Each PDX Mouse Model, and the Relationship Thereof with the Anti-Tumor Activity of Antibody-Drug Conjugate (1)

Data on the amount of gene expression in each PDX model used in Example 4 were obtained by the next-generation RNA sequencing method using RNA extracted from formalin-fixed paraffin-embedded specimens of each tumor. After the obtained data were normalized to a FPKM value, 1 was added to FPKM, and the sum was transformed to a logarithmic ($\log_2$) to obtain a $\log_2$[FPKM+1] value (Table 6). The $\log_2$[FPKM+1] value was used to analyze the relationship between the anti-tumor activity of antibody-drug conjugate (1) in each PDX model (Table 5) and the amount of expression of the hTROP2 gene and the SLFN11 gene. When all of the evaluated models were grouped into groups having at least a certain amount of expression of the hTROP2 and SLFN11 genes (Table 7), it was shown that the proportion of animal models showing at least a certain drug efficacy (in this case, a criterion of TGI of 75% or more was employed as an example) is higher as the hTROP2 gene expression and the SLFN11 gene expression increases (Table 8). In the absence of grouping by SLFN11 gene expression, the proportion of animal models showing TGI of 75% or more was not more than 43 to 50%. Thus, it was revealed that a combination of the amount of hTROP2 gene expression and the amount of SLFN11 gene expression can be used as a sensitivity marker to predict the anti-tumor effect of antibody-drug conjugate (1). For example, when the $\log_2$[FPKM+1] value of the hTROP2 gene exceeds 7.0 and the $\log_2$[FPKM+1] value of the SLFN11 gene exceeds 2.0, or when the $\log_2$[FPKM+1] value of the hTROP2 gene exceeds 6.0 and the $\log_2$[FPKM+1] of the SLFN11 gene exceeds 3.0, the proportion of animal models in which TGI is indicated to be 75% or more is about 80% to 100%. Furthermore, when the $\log_2$[FPKM+1] value of the hTROP2 gene exceeds 7.0 and the $\log_2$[FPKM+1] value of the SLFN11 gene exceeds 3.0, the proportion of animal models showing TGI of 75% or more is 100%. It should be noted that even when TGI was 70% or more or 80% or more, it was possible to predict anti-tumor effects at comparable prediction rates using each $\log_2$[FPKM+1] value which was specified when TGI was 75% or more.

TABLE 6 hTROP2 gene and SLFN11 gene expression in each PDX model

| Model ID | hTROP2 gene expression amount ($\log_2$ [FPKM + 1]) | SLFN11 gene expression amount ($\log_2$ [FPKM + 1]) |
|---|---|---|
| #1 | 7.56 | 1.25 |
| #2 | 8.00 | 2.39 |
| #3 | 7.15 | 1.71 |
| #4 | 7.40 | 0.59 |
| #5 | 6.79 | 0.13 |
| #6 | 6.30 | 0.15 |
| #7 | 4.67 | 1.82 |
| #8 | 6.52 | 2.99 |
| #9 | 6.75 | 5.06 |
| #10 | 7.57 | 2.99 |
| #11 | 7.32 | 4.20 |
| #12 | 7.11 | 2.69 |
| #13 | 3.85 | 5.02 |
| #14 | 7.73 | 3.11 |
| #15 | 7.02 | 0.00 |
| #16 | 7.08 | 1.06 |
| #17 | 6.09 | 2.70 |
| #18 | 7.70 | 1.06 |
| #19 | 5.57 | 3.40 |
| #20 | 6.83 | 1.28 |
| #21 | 7.69 | 0.64 |
| #22 | 7.69 | 4.17 |
| #23 | 7.10 | 0.05 |
| #24 | 6.67 | 0.00 |
| #25 | 6.54 | 4.07 |
| #26 | 5.89 | 0.00 |
| #27 | 5.48 | 0.08 |
| #28 | 6.38 | 2.28 |

TABLE 6-continued hTROP2 gene and SLFN11 gene expression in each PDX model

| Model ID | hTROP2 gene expression amount ($\log_2$ [FPKM + 1]) | SLFN11 gene expression amount ($\log_2$ [FPKM + 1]) |
|---|---|---|
| #29 | 7.97 | 3.56 |
| #30 | 1.64 | 4.23 |
| #31 | 5.71 | 0.00 |
| #32 | 4.84 | 3.87 |
| #33 | 2.78 | 5.30 |
| #34 | 4.99 | 5.40 |
| #35 | 7.02 | 0.01 |

TABLE 7

Number of PDX models having at least a certain amount of expression of the hTROP2 gene and the SLFN11 gene

| hTROP2 gene expression amount ($\log_2$ [FPKM + 1]) | SLFN11 gene expression amount ($\log_2$ [FPKM + 1]) | | | |
|---|---|---|---|---|
| | All models | >1 | >2 | >3 |
| All models | 35 | 24 | 18 | 12 |
| >4.0 | 32 | 21 | 15 | 9 |
| >5.0 | 29 | 18 | 13 | 7 |
| >6.0 | 25 | 17 | 12 | 6 |
| >7.0 | 16 | 11 | 7 | 4 |

TABLE 8

Proportion of PDX models showing TGI of 75% or more by antibody-drug conjugate (1) in PDX models having at least a certain amount of expression of the hTROP2 gene and the SLFN11 gene

| hTROP2 gene expression amount ($\log_2$ [FPKM + 1]) | SLFN11 gene expression amount ($\log_2$ [FPKM + 1]) | | | |
|---|---|---|---|---|
| | All models | >1 | >2 | >3 |
| All models | 43% | 54% | 56% | 58% |
| >4.0 | 44% | 57% | 60% | 67% |
| >5.0 | 41% | 56% | 62% | 71% |
| >6.0 | 48% | 59% | 67% | 83% |
| >7.0 | 50% | 64% | 86% | 100% |

Example 6. Production of Compound (1)

A compound represented by the formula:

[Formula 8]

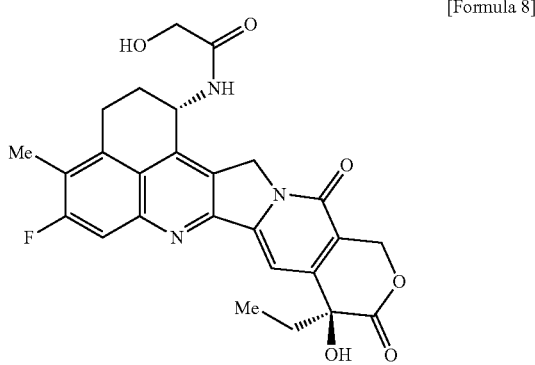 [SMILES: CC[C@@]1(O)C(=O)OCc2c1cc1n(c2=O)Cc2c-1nc1cc(F)c(C)c3c1c2[C@@H](NC(=O)CO)CC3]

(hereinafter, referred to as "compound (1)") was produced in accordance with the production methods described in WO 2014/057687 and WO 2015/115091.

Example 7. Cell Proliferation Inhibition Test Upon SLFN11 Knockdown 7-(1): Effect on Human Pharyngeal Cancer Cell Line FaDu Human pharyngeal cancer cell line FaDu was obtained from ATCC and used for evaluation. FaDu cells suspended at $2 \times 10^3$ cells/mL in a MEM medium containing a non-essential amino acid solution, a pyruvic acid solution and 10% bovine fetal serum were seeded in a 10 cm cell culture dish at 10 mL/dish. Twenty-four hours after seeding, 100 pmol of ON-TARGETplus SLFN11 siRNA (Dharmacon Inc.) or ON-TARGETplus Non-targeting Control Pool (Dharmacon Inc.) and 30 µL of Lipofectamine™ RNAiMAX Transfection Reagent (Thermo Fisher Scientific Inc.) were suspended in 1 mL of Opti-MEM medium, and the entire amount of the suspension was added to the medium. After 72 hours, the medium was removed and the dish was washed with PBS, then the cells were dissociated and recovered from the dish using 1 mL of TrypLE™ Express. The recovered cells were suspended at $5 \times 10^4$ cells/mL in a MEM medium containing a non-essential amino acid solution, a pyruvic acid solution and 10% bovine fetal serum, and were seeded in a 96-well cell culture plate at 100 µL/well. Twenty-four hours after seeding, the medium was replaced with a medium containing 100 nM, 33 nM, 11 nM, 3.7 nM, 1.2 nM, 0.41 nM, 0.13 nM, 0.045 nM, or 0 nM of compound (1) or antibody-drug conjugate (1) at 100 µL/well. The molar concentration of antibody-drug conjugate (1) was calculated by setting the average molecular weight to 150,000. Cells were all cultured at 37° C. under 5% $CO_2$. After 72 hours from the medium replacement, ATPlite 1 step detection system (PerkinElmer Inc.) was added at 100 µL/well. The wells were incubated at room temperature for 10 minutes, then the luminescence intensity of each well was measured.

The cell growth inhibition rate(%) at each condition was calculated using the following calculation formula:

Cell growth inhibition rate (%)=100×(1−$T/C$)

T: Average luminescence intensity of each well to which specimen was added
C: Average luminescence intensity of each well to which 0 nM specimen was added The 50% inhibitory concentration at each condition was calculated by fitting to the following calculation formula:

Cell viability (%)=($E$max−$E$min)×Specimen concentration$^\gamma$/(($E$max−50)/(50−$E$min)×IC50$^\gamma$+ Specimen concentration$^\gamma$)+$E$min Emax: maximum cell growth inhibition rate (%)
Emin: minimum cell growth inhibition rate (%)
IC50: 50% inhibitory concentration
γ: Hill coefficient The fitting to the calculation formula was performed using SAS Systems Release 9.2 (SAS Institute Inc.).

The cell proliferation inhibitory effects of compound (1) or antibody-drug conjugate (1) in FaDu cells upon SLFN11 knockdown are shown in FIG. 4. Each calculated 50% inhibitory concentration is shown in Table 9. The cell proliferation inhibitory effects of compound (1) and antibody-drug conjugate (1) were attenuated by SLFN11 knockdown in FaDu cell lines.

TABLE 9

Cell proliferation 50% inhibitory concentrations of compound (1) and antibody-drug conjugate (1) upon SLFN11 knockdown in FaDu cells, and fold change thereof

| Specimen | IC50 (nM) | | Fold change |
| --- | --- | --- | --- |
| | Non-targeting Control Pool | SLFN11 siRNA | (SLFN11/Non-targeting Control) |
| Compound (1) | 3.6 | 30.8 | 8.6 |
| Antibody-drug conjugate (1) | 42.6 | >100 | >2.3 |

7-(2): Effect on Human Lung Cancer Cell Line NCI-H1781

Human lung cancer cell line NCI-H1781 was obtained from ATCC and used for evaluation. NCI-H1781 cells suspended at $2\times10^3$ cells/mL in RPMI-1640 medium containing 10% bovine fetal serum were seeded in a 10 cm cell culture dish at 10 mL/dish. Twenty-four hours after seeding, 100 pmol of ON-TARGETplus SLFN11 siRNA (Dharmacon Inc.) or ON-TARGETplus Non-targeting Control Pool (Dharmacon Inc.) and 30 μL of Lipofectamine™ RNAiMAX Transfection Reagent (Thermo Fisher Scientific Inc.) were suspended in 1 mL of Opti-MEM medium, and the entire amount of the suspension was added to the medium. After 72 hours, the medium was removed and the dish was washed with PBS, then the cells were dissociated and recovered from the dish using 1 mL of TrypLE™ Express. The recovered cells were suspended at $5\times10^4$ cells/mL in RPMI-1640 medium containing 10% bovine fetal serum, and seeded in a 96-well cell culture plate at 100 μL/well. Twenty-four hours after seeding, the medium was replaced with a medium containing 100 nM, 33 nM, 11 nM, 3.7 nM, 1.2 nM, 0.41 nM, 0.13 nM, 0.045 nM, or 0 nM of compound (1) or antibody-drug conjugate (1) at 100 μL/well. The molar concentration of antibody-drug conjugate (1) was calculated by setting the average molecular weight to 150,000. Cells were all cultured at 37° C. under 5% $CO_2$. After 72 hours from the medium replacement, ATPlite 1 step detection system (PerkinElmer Inc.) was added at 100 μL/well. The wells were incubated at room temperature for 10 minutes, then the luminescence intensity of each well was measured.

The cell growth inhibition rate (%) at each condition was calculated using the following calculation formula:

Cell growth inhibition rate (%)=100×(1−T/C)

T: Average luminescence intensity of each well to which specimen was added
C: Average luminescence intensity of each well to which 0 nM specimen was added The 50% inhibitory concentration at each condition was calculated by fitting to the following calculation formula:

Cell viability (%)=(Emax−Emin)×Specimen concentration$^\gamma$/((Emax−50)/(50−Emin)×IC50$^\gamma$+ Specimen concentration$^\gamma$)+Emin Emax: maximum cell growth inhibition rate (%)
Emin: minimum cell growth inhibition rate (%)
IC50: 50% inhibitory concentration
γ: Hill coefficient The fitting to the calculation formula was performed using SAS Systems Release 9.2 (SAS Institute Inc.).

The cell proliferation inhibitory effects of compound (1) or antibody-drug conjugate (1) in NCI-H1781 cells upon SLFN11 knockdown are shown in FIG. 5. Each calculated 50% inhibitory concentration is shown in Table 10. The cell proliferation inhibitory effects of compound (1) and antibody-drug conjugate (1) were attenuated by SLFN11 knockdown in NCI-H1781 cell lines.

TABLE 10

Cell proliferation 50% inhibitory concentrations of compound (1) and antibody-drug conjugate (1) upon SLFN11 knockdown in NCI-H1781 cells, and fold change thereof

| Specimen | IC50 (nM) | | Fold change |
| --- | --- | --- | --- |
| | Non-targeting Control Pool | SLFN11 siRNA | (SLFN11/Non-targeting Control) |
| Compound (1) | 3.3 | 15 | 4.5 |
| Antibody-drug conjugate (1) | 8 | >100 | >12.5 |

7-(3): Effect on Human Lung Cancer Cell Line Calu-3

Human lung cancer cell line Calu-3 was obtained from ATCC and used for evaluation. Calu-3 cells suspended at $2\times10^3$ cells/mL in a MEM medium containing a non-essential amino acid solution, a pyruvic acid solution and 10% bovine fetal serum were seeded in a 10 cm cell culture dish at 10 mL/dish. Twenty-four hours after seeding, 100 pmol of ON-TARGETplus SLFN11 siRNA (Dharmacon Inc.) or ON-TARGETplus Non-targeting Control Pool (Dharmacon Inc.) and 30 μL of Lipofectamine™ RNAiMAX Transfection Reagent (Thermo Fisher Scientific Inc.) were suspended in 1 mL of Opti-MEM medium, and the entire amount of the suspension was added to the medium. After 72 hours, the medium was removed and the dish was washed with PBS, then the cells were dissociated and recovered from the dish using 1 mL of TrypLE™ Express. The recovered cells were suspended at $5\times10^4$ cells/mL in a MEM medium containing a non-essential amino acid solution, a pyruvic acid solution and 10% bovine fetal serum, and seeded in a 96-well cell culture plate at 100 μL/well. Twenty-four hours after seeding, the medium was replaced with a medium containing 100 nM, 33 nM, 11 nM, 3.7 nM, 1.2 nM, 0.41 nM, 0.13 nM, 0.045 nM, or 0 nM of compound (1) or antibody-drug conjugate (1) at 100 μL/well. The molar concentration of antibody-drug conjugate (1) was calculated by setting the average molecular weight to 150,000. Cells were all cultured at 37° C. under 5% $CO_2$. After 72 hours from the medium replacement, ATPlite 1 step detection system (PerkinElmer Inc.) was added at 100 μL/well. The wells were incubated at room temperature for 10 minutes, then the luminescence intensity of each well was measured.

The cell growth inhibition rate (%) at each condition was calculated using the following calculation formula:

Cell growth inhibition rate (%)=100×(1−T/C)

T: Average luminescence intensity of each well to which specimen was added
C: Average luminescence intensity of each well to which 0 nM specimen was added The 50% inhibitory concentration at each condition was calculated by fitting to the following calculation formula:

Cell viability (%)=(Emax−Emin)×Specimen concentration$^\gamma$/((Emax−50)/(50−Emin)×IC50$^\gamma$+ Specimen concentration$^\gamma$)+Emin Emax: maximum cell growth inhibition rate (%)
Emin: minimum cell growth inhibition rate (%)
IC50: 50% inhibitory concentration
γ: Hill coefficient The fitting to the calculation formula was performed using SAS Systems Release 9.2 (SAS Institute Inc.).

The cell proliferation inhibitory effects of compound (1) or antibody-drug conjugate (1) in Calu-3 cells upon SLFN11 knockdown are shown in FIG. 6. Each calculated 50% inhibitory concentration is shown in Table 11. The cell proliferation inhibitory effect of compound (1) was attenuated by SLFN11 knockdown in Calu-3 cell lines.

TABLE 11

Cell proliferation 50% inhibitory concentrations of compound (1) and antibody-drug conjugate (1) upon SLFN11 knockdown in Calu-3 cells, and fold change thereof

| Specimen | IC50 (nM) | | Fold change |
| --- | --- | --- | --- |
|  | Non-targeting Control Pool | SLFN11 siRNA | (SLFN11/Non-targeting Control) |
| Compound (1) | 20.9 | >100 | >4.8 |
| Antibody-drug conjugate (1) | >100 | >100 | — |

7-(4): Effect on Human Breast Cancer Cell Line MDA-MB-468

Human breast cancer cell line MDA-MB-468 was obtained from ATCC and used for evaluation. MDA-MB-468 cells suspended at $2 \times 10^3$ cells/mL in RPMI-1640 medium containing 10% bovine fetal serum were seeded in a 10 cm cell culture dish at 10 mL/dish. Twenty-four hours after seeding, 100 μmol of ON-TARGETplus SLFN11 siRNA (Dharmacon Inc.) or ON-TARGETplus Non-targeting Control Pool (Dharmacon Inc.) and 30 μL of Lipofectamine™ RNAiMAX Transfection Reagent (Thermo Fisher Scientific Inc.) were suspended in 1 mL of Opti-MEM medium, and the entire amount of the suspension was added to the medium. After 72 hours, the medium was removed and the dish was washed with PBS, then the cells were dissociated and recovered from the dish using 1 mL of TrypLE™ Express. The recovered cells were suspended at $5 \times 10^4$ cells/mL in RPMI-1640 medium containing 10% bovine fetal serum, and seeded in a 96-well cell culture plate at 100 μL/well. Twenty-four hours after seeding, the medium was replaced with a medium containing 100 nM, 33 nM, 11 nM, 3.7 nM, 1.2 nM, 0.41 nM, 0.13 nM, 0.045 nM, or 0 nM of compound (1) or antibody-drug conjugate (1) at 100 μL/well. The molar concentration of antibody-drug conjugate (1) was calculated by setting the average molecular weight to 150,000. Cells were all cultured at 37° C. under 5% $CO_2$. After 72 hours from the medium replacement, ATPlite 1 step detection system (PerkinElmer Inc.) was added at 100 μL/well. The wells were incubated at room temperature for 10 minutes, then the luminescence intensity of each well was measured.

The cell growth inhibition rate (%) at each condition was calculated using the following calculation formula:

Cell growth inhibition rate (%)=100×(1−T/C)

T: Average luminescence intensity of each well to which specimen was added
C: Average luminescence intensity of each well to which 0 nM specimen was added The 50% inhibitory concentration at each condition was calculated by fitting to the following calculation formula:

Cell viability (%)=($E$max−$E$min)×Specimen concentration$^\gamma$/(($E$max−50)/(50−$E$min)×IC50$^\gamma$+ Specimen concentration$^\gamma$)+$E$min Emax: maximum cell growth inhibition rate (%)
Emin: minimum cell growth inhibition rate (%)
IC50: 50% inhibitory concentration
γ: Hill coefficient The fitting to the calculation formula was performed using SAS Systems Release 9.2 (SAS Institute Inc.).

The cell proliferation inhibitory effects of compound (1) or antibody-drug conjugate (1) in MDA-MB-468 cells upon SLFN11 knockdown are shown in FIG. 7. Each calculated 50% inhibitory concentration is shown in Table 12. The cell proliferation inhibitory effect of compound (1) was attenuated by SLFN11 knockdown in MDA-MB-468 cell lines.

TABLE 12

Cell proliferation 50% inhibitory concentrations of compound (1) and antibody-drug conjugate (1) upon SLFN11 knockdown in MDA-MB-468 cells, and fold change thereof

| Specimen | IC50 (nM) | | Fold change |
| --- | --- | --- | --- |
|  | Non-targeting Control Pool | SLFN11 siRNA | (SLFN11/Non-targeting Control) |
| Compound (1) | 4.8 | 27.5 | 5.7 |
| Antibody-drug conjugate (1) | >100 | >100 | — |

7-(5): Effect on Human Breast Cancer Cell Line HCC38

Human breast cancer cell line HCC38 was obtained from ATCC and used for evaluation. HCC38 cells suspended at $2 \times 10^5$ cells/mL in RPMI-1640 medium containing 10% bovine fetal serum were seeded in a 10 cm cell culture dish at 10 mL/dish. Twenty-four hours after seeding, 100 pmol of ON-TARGETplus SLFN11 siRNA (Dharmacon Inc.) or ON-TARGETplus Non-targeting Control Pool (Dharmacon Inc.) and 30 μL of Lipofectamine™ RNAiMAX Transfection Reagent (Thermo Fisher Scientific Inc.) were suspended in 1 mL of Opti-MEM medium, and the entire amount of the suspension was added to the medium. After 72 hours, the medium was removed and the dish was washed with PBS, then the cells were dissociated and recovered from the dish using 1 mL of TrypLE™ Express. The recovered cells were suspended at $5 \times 10^4$ cells/mL in RPMI-1640 medium containing 10% bovine fetal serum, and seeded in a 96-well cell culture plate at 100 μL/well. Twenty-four hours after seeding, the medium was replaced with a medium containing 100 nM, 33 nM, 11 nM, 3.7 nM, 1.2 nM, 0.41 nM, 0.13 nM, 0.045 nM, or 0 nM of compound (1) or antibody-drug conjugate (1) at 100 μL/well. The molar concentration of antibody-drug conjugate (1) was calculated by setting the average molecular weight to 150,000. Cells were all cultured at 37° C. under 5% $CO_2$. After 72 hours from the medium replacement, ATPlite 1 step detection system (PerkinElmer Inc.) was added at 100 μL/well. The wells were incubated at room temperature for 10 minutes, then the luminescence intensity of each well was measured.

The cell growth inhibition rate (%) at each condition was calculated using the following calculation formula:

Cell growth inhibition rate (%)=100×(1−T/C)

T: Average luminescence intensity of each well to which specimen was added
C: Average luminescence intensity of each well to which 0 nM specimen was added The 50% inhibitory concentration at each condition was calculated by fitting to the following calculation formula:

Cell viability (%)=($E$max−$E$min)×Specimen concentration$^\gamma$/(($max$−50)/(50−$E$min)×IC50$^\gamma$+ Specimen concentration$^\gamma$)+$E$min Emax: maximum cell growth inhibition rate (%)
Emin: minimum cell growth inhibition rate (%)
IC50: 50% inhibitory concentration
γ: Hill coefficient The fitting to the calculation formula was performed using SAS Systems Release 9.2 (SAS Institute Inc.).

The cell proliferation inhibitory effects of compound (1) or antibody-drug conjugate (1) in HCC38 cells upon SLFN11 knockdown are shown in FIG. 8. Each calculated 50% inhibitory concentration is shown in Table 13. The cell proliferation inhibitory effects of compound (1) and antibody-drug conjugate (1) were attenuated by SLFN11 knockdown in HCC38 cell lines.

TABLE 13

Cell proliferation 50% inhibitory concentrations of compound (1) and antibody-drug conjugate (1) upon SLFN11 knockdown in HCC38 cells, and fold change thereof

| Specimen | IC50 (nM) | | Fold change |
|---|---|---|---|
| | Non-targeting Control Pool | SLFN11 siRNA | (SLFN11/Non-targeting Control) |
| Compound (1) | 1.6 | 4.2 | 2.6 |
| Antibody-drug conjugate (1) | 56.7 | >100 | >1.8 |

Example 8. hTROP2 and SLFN11 Gene Expression (Median Normalized Count Values) of Tumors Derived from Each Patient in a Clinical Trial, and the Relationship Between the Amount of Expression with the Anti-Tumor Activity of Antibody-Drug Conjugate (1)

8-(1) Study Plan and Drug Effect

In a dose escalation part of a Phase 1 study for patients with relapsed and advanced non-small cell lung cancer, the antibody-drug conjugate (1) was administered intravenously once every three weeks until unacceptable toxicity or worsening of the pathological condition was observed. The dose-limiting toxicity was determined in Cycle 1 (Days 1-21). Tumor sampling was performed after entry into the clinical study following the first dose. The dose administered and the maximum tumor change rate(%) in each patient are shown in Table 14. Note that a minus value in the maximum tumor change rate means that the tumor has been reduced by administration of antibody-drug conjugate (1).

8-(2) Measurement of SLFN11, TROP2 mRNA Levels in Tumors

Gene expression data of each patient were obtained by EdgeSeq after preparing a section from a formalin-fixed paraffin-embedded specimen of tumor tissue of each patient prior to antibody-drug conjugate (1) administration, and cutting out a tumor site by laser microdissection. The obtained count data were normalized by the Median normalization method, thereby the amount of expression of each gene was obtained. All the above tests were performed at HTG Molecular Diagnostics, Inc.

To the Median Normalized Count (MNC) value, after being obtained and normalized at HTG Molecular Diagnostics, Inc., 1 was added, and the sum was transformed to a logarithmic ($\log_2$) to obtain a $\log_2$[MNC+1] value (Table 15). The $\log_2$[MNC+1] value was used to analyze the relationship between the anti-tumor activity of antibody-drug conjugate (1) in each patient (Table 14) and the amount of expression of the hTROP2 gene and the SLFN11 gene. When all of the evaluated patients were grouped into groups having at least a certain amount of expression of the hTROP2 and SLFN11 genes (Table 16), it was shown that the proportion of patients showing at least a certain drug efficacy (maximum tumor change rate of 0% or less) is higher as the hTROP2 gene expression and the SLFN11 gene expression increases (Table 17). In the absence of grouping by SLFN11 gene expression, the proportion of patients showing the maximum tumor change rate of 0% or less was not more than 75 to 80%. Thus, it was revealed that a combination of the amount of hTROP2 gene expression and the amount of SLFN11 gene expression can be used as a sensitivity marker to predict the anti-tumor effect of antibody-drug conjugate (1). For example, when the $\log_2$[MNC+1] value of the hTROP2 gene exceeds 12 and the $\log_2$[MNC+1] value of the SLFN11 gene exceeds 11.5, the proportion of patients in which the maximum tumor change rate is 0% or less is about 80% to 100%.

TABLE 14

Anti-tumor activity of antibody-drug conjugate (1) in each patient (maximum tumor change rate)

| Patient ID | Antibody-drug conjugate dose (mg/kg) | Maximum tumor change rate (%) |
|---|---|---|
| #1 | 2 | −7.14 |
| #2 | 2 | −68.52 |
| #3 | 2 | −4.76 |
| #4 | 2 | −11.70 |
| #5 | 2 | 52.00 |
| #6 | 2 | 3.15 |
| #7 | 4 | 33.33 |
| #8 | 4 | −53.13 |
| #9 | 6 | −52.27 |
| #10 | 8 | −3.47 |
| #11 | 8 | −35.46 |
| #12 | 8 | −63.64 |

TABLE 15 hTROP2 gene and SLFN11 gene expression in each patient

| Patient ID | hTROP2 gene expression amount ($\log_2$ [MNC + 1]) | SLFN11 gene expression amount ($\log_2$ [MNC + 1]) |
|---|---|---|
| #1 | 14.32 | 13.13 |
| #2 | 14.34 | 12.32 |
| #3 | 12.94 | 12.32 |
| #4 | 14.80 | 12.90 |
| #5 | 12.55 | 11.35 |
| #6 | 16.59 | 12.25 |
| #7 | 10.10 | 11.69 |
| #8 | 11.35 | 12.24 |
| #9 | 12.14 | 12.73 |
| #10 | 11.56 | 13.28 |
| #11 | 15.18 | 11.99 |
| #12 | 13.08 | 12.85 |

TABLE 16

Number of patients having at least a certain amount of expression of the hTROP2 gene and the SLFN11 gene

| hTROP2 gene expression amount | SLFN11 gene expression amount ($\log_2$ [MNC + 1]) | | |
|---|---|---|---|
| ($\log_2$ [MNC + 1]) | All models | >11.5 | >12.5 |
| All models | 12 | 11 | 5 |
| >12 | 9 | 8 | 4 |
| >14 | 5 | 5 | 2 |

TABLE 17

Proportion of patients showing a maximum tumor change rate of 0% or less by antibody-drug conjugate (1) in patients having at least a certain amount of expression of the hTROP2 gene and the SLFN11 gene

| hTROP2 gene expression amount | SLFN11 gene expression amount ($\log_2$ [MNC + 1]) | | |
|---|---|---|---|
| ($\log_2$ [MNC + 1]) | All models | >11.5 | >12.5 |
| All models | 75% | 82% | 100% |
| >12 | 78% | 88% | 100% |
| >14 | 80% | 80% | 100% |

Free Text of Sequence Listing

SEQ ID NO: 1: Amino acid sequence of the heavy chain of a humanized anti-hTROP2 antibody
SEQ ID NO: 2: Amino acid sequence of the light chain of a humanized anti-hTROP2 antibody
SEQ ID NO: 3: CDRH1 sequence of the heavy chain of a humanized anti-hTROP2 antibody
SEQ ID NO: 4: CDRH2 sequence of the heavy chain of a humanized anti-hTROP2 antibody
SEQ ID NO: 5: CDRH3 sequence of the heavy chain of a humanized anti-hTROP2 antibody
SEQ ID NO: 6: CDRL1 sequence of the light chain of a humanized anti-hTROP2 antibody
SEQ ID NO: 7: CDRL2 sequence of the light chain of a humanized anti-hTROP2 antibody
SEQ ID NO: 8: CDRL3 sequence of the light chain of a humanized anti-hTROP2 antibody

The invention claimed is:

1. A method for identifying a subject to whom a medicament containing an anti-hTROP2 antibody-drug conjugate is to be given, wherein the subject is a human patient suffering from a cancer, the method comprising:
   1) obtaining a biological sample from the human patient diagnosed as suffering from a cancer;
   2) evaluating an amount of expression of the hTROP2 gene at mRNA level in the biological sample;
   3) evaluating an amount of expression of the SLFN11 gene at mRNA level in the biological sample, wherein the biological sample is one that is determined to have a high amount of expression of the hTROP2 gene; and
   4) identifying the human patient who provided the biological sample, wherein the biological sample is one that is determined to have a high amount of expression of the SLFN11 gene, as a subject to whom an anti-hTROP2 antibody-drug conjugate is to be given,
   wherein the drug portion of the anti-hTROP2 antibody-drug conjugate comprises a topoisomerase I inhibitor,
   wherein a $\log_2[\text{FPKM}+1]$ value is measured by RNA sequencing from the biological sample obtained from the human patient diagnosed as suffering from a cancer,
   wherein the biological sample is determined to have a high amount of expression of the hTROP2 gene at mRNA level when the $\log_2[\text{FPKM}+1]$ value exceeds 6.0,
   wherein the biological sample is determined to have a high amount of expression of the SLFN11 gene at mRNA level when the $\log_2[\text{FPKM}+1]$ value exceeds 2.0, and
   the subject identified in step 4) is treated with the anti-hTROP2 antibody-drug conjugate.

2. The method according to claim 1, wherein the biological sample is determined to have a high amount of expression of the hTROP2 gene at mRNA level when the $\log_2[\text{FPKM}+1]$ value exceeds any one selected from the group consisting of 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0.

3. The method according to claim 1, wherein the biological sample is determined to have a high amount of expression of the hTROP2 gene at mRNA level when the $\log_2[\text{FPKM}+1]$ value exceeds any one selected from the group consisting of 6.1, 6.2, 6.3, 6.4, 6.5, 6.6, 6.7, 6.8, 6.9, and 7.0.

4. The method according to claim 1, wherein the biological sample is determined to have a high amount of expression of the hTROP2 gene at mRNA level when the $\log_2[\text{FPKM}+1]$ value exceeds 7.0.

5. The method according to claim 1, wherein the biological sample is determined to have a high amount of expression of the SLFN11 gene at mRNA level when the $\log_2[\text{FPKM}+1]$ value exceeds any one selected from the group consisting of 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0.

6. The method according to claim 1, wherein the biological sample is determined to have a high amount of expression of the SLFN11 gene at mRNA level when the $\log_2[\text{FPKM}+1]$ value exceeds any one selected from the group consisting of 2.1, 2.2, 2.3, 2.4, 2.5, 2.6, 2.7, 2.8, 2.9, and 3.0.

7. The method according to claim 1, wherein the biological sample is determined to have a high amount of expression of the SLFN11 gene at mRNA level when the $\log_2[\text{FPKM}+1]$ value exceeds 3.0.

8. The method according to claim 1, wherein the biological sample includes a tumor sample.

9. The method according to claim 1, wherein the anti-hTROP2 antibody-drug conjugate is an antibody-drug conjugate in which a drug-linker is shown by the formula:

[Formula 1]

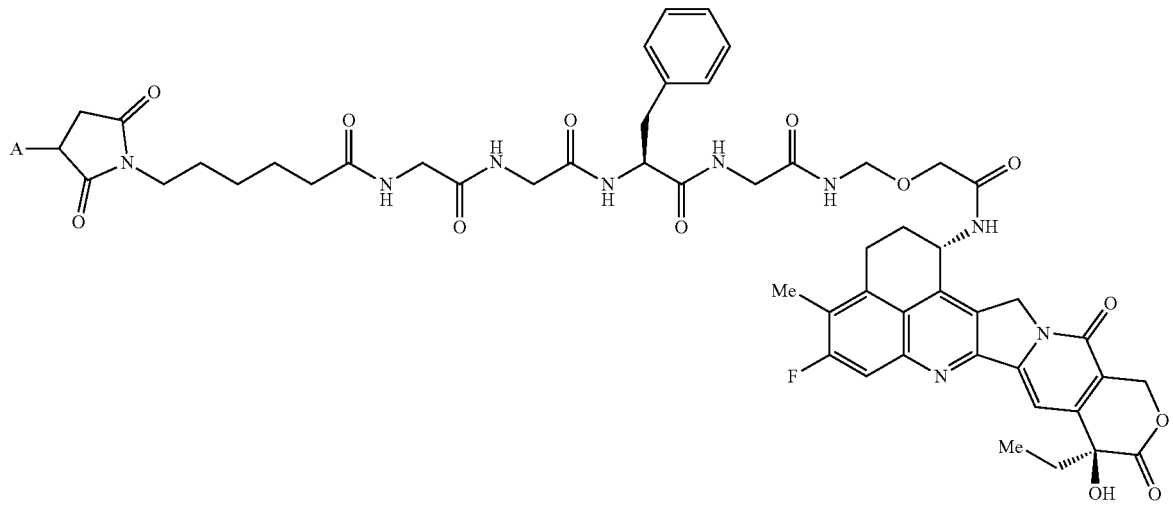

wherein A represents a connecting position to the anti-hTROP2 antibody,
and the anti-hTROP2 antibody and linker moiety of the drug-linker are conjugated to each other via a thioether bond.

10. The method according to claim 9, wherein the anti-hTROP2 antibody is an antibody consisting of a heavy chain consisting of an amino acid sequence consisting of amino acid residues 20 to 470 of SEQ ID NO: 1 and a light chain consisting of an amino acid sequence consisting of amino acid residues 21 to 234 of SEQ ID NO: 2.

11. The method according to claim 9, wherein the anti-hTROP2 antibody is an antibody consisting of a heavy chain consisting of an amino acid sequence consisting of amino acid residues 20 to 470 of SEQ ID NO: 1 and a light chain consisting of an amino acid sequence consisting of amino acid residues 21 to 234 of SEQ ID NO: 2, and wherein a lysine residue at the carboxyl terminus of the heavy chain of the anti-hTROP2 antibody is deleted.

12. The method according to claim 9, wherein an average number of units of the drug-linker conjugated per antibody molecule ranges from 2 to 8.

13. The method according to claim 9, wherein an average number of units of the drug-linker conjugated per antibody molecule ranges from 3.5 to 4.5.

14. The method according to claim 1, wherein the anti-hTROP2 antibody-drug conjugate is Sacituzumab Govitecan (IMMU-132).

15. The method according to claim 1, wherein the cancer is a lung cancer, a kidney cancer, a urothelial cancer, a colorectal cancer, a prostate cancer, polymorphic glioblastoma, an ovarian cancer, a pancreatic cancer, a breast cancer, melanoma, a liver cancer, a bladder cancer, a gastric cancer, a cervical cancer, a uterine cancer, a head and neck cancer, an esophageal cancer, a biliary tract cancer, a thyroid cancer, lymphoma, acute myeloid leukemia, acute lymphoid leukemia, or multiple myeloma.

16. A method for identifying a subject to whom a medicament containing an anti-hTROP2 antibody-drug conjugate is to be given, wherein the subject is a human patient suffering from a cancer, the method comprising:
1) obtaining a biological sample from the human patient diagnosed as suffering from a cancer;
2) evaluating an amount of expression of the hTROP2 gene and the SLFN11 gene at mRNA level in the biological sample; and
3) identifying the human patient who provided the biological sample, wherein the biological sample is one that is determined to have a high amount of expression of the hTROP2 gene and the SLFN11 gene, as a subject to whom an anti-hTROP2 antibody-drug conjugate is to be given,
wherein the drug portion of the anti-hTROP2 antibody-drug conjugate comprises a topoisomerase I inhibitor,
wherein a $\log_2[\text{FPKM}+1]$ value is measured by RNA sequencing from the biological sample obtained from the human patient diagnosed as suffering from a cancer,
wherein the biological sample is determined to have a high amount of expression of the hTROP2 gene at mRNA level when the $\log_2[\text{FPKM}+1]$ value exceeds 6.0, and
wherein the biological sample is determined to have a high amount of expression of the SLFN11 gene at mRNA level when the $\log_2[\text{FPKM}+1]$ value exceeds 2.0, and
the subject identified in step 3) is treated with the anti-hTROP2 antibody-drug conjugate.

17. The method according to claim 16, wherein a $\log_2[\text{FPKM}+1]$ value is measured by RNA sequencing from the biological sample obtained from the human patient diagnosed as suffering from a cancer, wherein the biological sample is determined to have a high amount of expression of the hTROP2 gene at mRNA level when the $\log_2[\text{FPKM}+1]$ value exceeds any one selected from the group consisting of 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0,
and wherein the biological sample is determined to have a high amount of expression of the SLFN11 gene at mRNA level when the $\log_2[\text{FPKM}+1]$ value exceeds any one selected from the group consisting of 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0.

18. The method according to claim 16, wherein the biological sample includes a tumor sample.

19. The method according to claim 16, wherein the cancer is a lung cancer, a kidney cancer, a urothelial cancer, a colorectal cancer, a prostate cancer, polymorphic glioblastoma, an ovarian cancer, a pancreatic cancer, a breast cancer, melanoma, a liver cancer, a bladder cancer, a gastric cancer, a cervical cancer, a uterine cancer, a head and neck cancer, an esophageal cancer, a biliary tract cancer, a thyroid cancer, lymphoma, acute myeloid leukemia, acute lymphoid leukemia, and/or multiple myeloma.

20. A method for treating a subject suffering from a cancer, comprising:
    identifying a subject having (i) a high amount of expression of the hTROP2 gene at mRNA level; and (ii) a high amount of expression of the SLFN11 gene at mRNA level by evaluating an amount of expression of the SLFN11 gene at mRNA level and hTROP2 gene at mRNA level in a biological sample obtained from the subject, and
    administering to the subject an effective amount of the anti-hTROP2 antibody-drug conjugate, wherein the drug portion of the anti-hTROP2 antibody-drug conjugate comprises a topoisomerase I inhibitor,
    wherein the high amount of expression of the hTROP2 gene at mRNA level is when a $\log_2[\text{FPKM}+1]$ value measured by RNA sequencing from the biological sample exceeds 6.0, and
    wherein the high amount of expression of the SLFN11 gene at mRNA level is when a $\log_2[\text{FPKM}+1]$ value measured by RNA sequencing from the biological sample exceeds 2.0.

* * * * *

UNITED STATES PATENT AND TRADEMARK OFFICE
CERTIFICATE OF CORRECTION

| | | |
|---|---|---|
| PATENT NO. | : 12,312,641 B2 | Page 1 of 1 |
| APPLICATION NO. | : 17/269615 | |
| DATED | : May 27, 2025 | |
| INVENTOR(S) | : Daisuke Okajima, Satoru Yasuda and Kei Enomoto | |

It is certified that error appears in the above-identified patent and that said Letters Patent is hereby corrected as shown below:

In the Claims

In Claim 19, Column 59, Line 7, please delete "and/or multiple myeloma" and replace with --or multiple myeloma--

Signed and Sealed this
Ninth Day of September, 2025

Coke Morgan Stewart
*Acting Director of the United States Patent and Trademark Office*